United States Patent [19]

Tsien et al.

[11] Patent Number: 5,866,548
[45] Date of Patent: Feb. 2, 1999

[54] CAGED MEMBRANE-PERMEANT INOSITOL PHOSPHATES

[75] Inventors: Roger Y. Tsien; Wenhong Li, both of La Jolla, Calif.

[73] Assignee: The Regents of the University of California, Oakland, Calif.

[21] Appl. No.: 769,665

[22] Filed: Dec. 19, 1996

Related U.S. Application Data

[63] Continuation-in-part of Ser. No. 475,758, Jun. 7, 1995, which is a continuation-in-part of Ser. No. 45,585, Apr. 9, 1993, Pat. No. 5,693,521.

[51] Int. Cl.$^6$ .............................. A61K 31/70; C07H 1/00; C07H 11/04; C07H 13/00
[52] U.S. Cl. ........................ 514/23; 514/144; 536/1.11; 536/117; 558/156; 558/160; 568/883
[58] Field of Search ................................... 536/1.11, 117; 558/156, 160; 568/883; 514/23, 144

[56] References Cited

U.S. PATENT DOCUMENTS

| | | | |
|---|---|---|---|
| 4,515,722 | 5/1985 | Yang et al. | 260/403 |
| 4,816,570 | 3/1989 | Farquhar | 536/26 |
| 4,968,788 | 11/1990 | Farquhar | 536/25 |
| 4,988,682 | 1/1991 | Kozikowski et al. | 514/150 |
| 5,053,399 | 10/1991 | Kozikowski et al. | 514/150 |
| 5,177,064 | 1/1993 | Bodor et al. | 514/51 |
| 5,210,263 | 5/1993 | Kozikowski et al. | 558/161 |
| 5,227,508 | 7/1993 | Kozikowski et al. | 558/155 |
| 5,428,163 | 6/1995 | Mills | 544/232 |

FOREIGN PATENT DOCUMENTS

| | | |
|---|---|---|
| 9423724 | 10/1994 | WIPO . |
| 9640695 | 12/1996 | WIPO . |

OTHER PUBLICATIONS

Vajanaphanich et al., "Long–Term Uncoupling of Chloride Secretion From Extracellular Calcium Levels by [Inositol] (3,4,5,6) P$_4$," *Nature*, 371, 711–714 (Oct. 20, 1994).

Roemer et al., "Synthesis of D–myo–Inositol 3,4,5,6–and 1,4,5,6–Tetrakisphosphate Analogues and Their Membrane–Permaant Derivatives," *J. Chem. Soc., Chem. Comm.*, (Issue No. 4), 411–412, (Feb. 21, 1995).

Schultz et al., "Acetoxymethyl esters of phosphates, enhancements of the permeability and potency of cAMP," *J. Bio. Chem.*, vol. 268, No. 9, pp. 6316–6322. (Mar. 25, 1993).

Tsien, R.Y., "Intracellular signal transduction in four dimensions: from molecular design to physiology," *Am. J. Physiology*, vol. 32, No. 4, C723–C728, (Oct. 1992).

Schultz et al., "Membrane–Permeant Derivatives of Inositol Polyphosphates Applied to REF–52 Fibroblasts," *The FASEB Journal*, p. A1924, Abstract No. 5819. (Apr. 4, 1992).

Berridge et al., "Inositol phosphates and cell signalling," *Nature*, vol. 341, 197–205, 1989., Sep. 21.

Shears, S.B., "Metabolism of the inositol phosphates produced upon receptor activation," *Biochem. J.* (1989) 260, 313–324.

Kaplan, A.T., "A possible role for inositool tetrakisphosphate as a negative regulator of calcium–related epithelial chloride secretion," Abstract Form for Aemrican Gastroenterological Association, May 1992.

Farquhar et al., "Biologically–reversible phosphate–protective groups," *J. Pharm. Sci.*, vol. 72, No. 3, pp. 324–325. (Mar. 1983).

Srivastva et al., "Bioreversible phosphate protective groups: synthesis and stability of model acyloxymethyl phosphates," *Bioorganic Chem.*, 12, 118–129 (1984).

Poirot et al., "Influence of the Absolute Configuration at C–4 in the Binding of D–Myo Inositol 1,4,5 Triphosphate Analogues to the IP$_3$ Receptor," *Bioorganic & Medicinal Chem. Lett.*, 5(6), 569–572 (1995).

Fauq et al., "Probing the D–1,4,5–IP$_3$/D–1,3,4,5–IP$_4$ Functional Interface. Synthesis and Pharmacology of Novel D–3–Modified myo–Inositol Trisphosphate Analogues," *J. Chem. Soc. Chem. Comm.*, (11), 1301–1302(7 Jun. 1994).

Seewald et al., "Synthesis of D–3–Deoxy–myo–Inositol 1,4,5–Trisphosphate and its Effect on Ca$^{2+}$ Release in the NIH 3T3 Cells," *J. Chem. Soc. Chem. Comm.*, (22), 1638–1639(15 Nov. 1990).

Kozikowski et al., "Deoxygenated Inositol 1,4,5–Trisphosphate Analogues and Their Interaction with Metabolic Enzymes. (1R, 2S, 4R)–Cyclohexane–1,2,4–tris(methylenesulfonate): A Potent Selective 5–Phosphate Inhibitor," *J. Medicinal Chem.*, 36(20), 3035–3038(1993).

Kozikowski et al., "Synthesis of ID–3–Deoxy–, 1D–2, 3–Dideoxy–, and 1D–2,3,6–Trideoxy–myo–inositol 1,4, 5–Tirsphosphate from Quebrachitol, Their Binding Affinities, and Calcium Release Activity," *J. Am Chem. Soc.*, 115(11), 4429–4434 (1993).

Walker et al., "Kinetics of smooth and skeletal muscle activation by laser pulse photolysis of caged inositol 1,4, 5–trisphosphate," *Nature*, vol. 327, 249–252. (May 21, 1987).

*Primary Examiner*—John Kight
*Assistant Examiner*—L. Eric Crane
*Attorney, Agent, or Firm*—Fish & Richardson P.C.

[57] ABSTRACT

Caged acyloxyalkyl esters of phosphate-containing inositol phosphates which are capable of permeating cell membranes. The second messengers are protected (caged) at the 6-hydroxyl, with a photolabile group. Once inside the cell, the ester derivatives undergo enzymatic conversion to remove the acyloxyalkyl ester groups. The resulting caged compound remains biologically inactive until exposed to ultraviolet (UV) light. Upon UV light exposure, the active form of the second messenger is released within the cell.

18 Claims, 16 Drawing Sheets

DOSE-RESPONSE RELATIONS FOR $Bt_2cAMP/AM$ (○) vs $Bt_2cAMP$ (●), 8-Br-cAMP (△) AND 8-pCPT-cAMP (▲).

(a). (1) $(CNCH_2CH_2O)_2PN(i\text{-}Pr)_2$, TETRAZOLE (2) $(PhC(O)S\text{-})_2$, $CH_2Cl_2$ (b) $NH_2OH$, MeOH
(c) PM-Br, DIEA/$CH_3CN$ (d) HOAc, TFA (cat)

(a) HOAc, TFA (cat)
(b) (1) (CNCH$_2$CH$_2$O)$_2$PN(i-Pr)$_2$, TETRAZOLE (2) tBuOOH, CH$_2$Cl$_2$ (c) NH$_4$OH, MeOH (d) PM-Br, DIEA/CH$_3$CN
(e) ACETIC ANHYDRIDE, PYRIDINE(cat)

CAGED MEMBRANE-PERMEANT INOSITOL PHOSPHATES

This is a continuation-in-part of application Ser. No. 08/475,758, filed Jun. 7, 1995 which is a continuation in part of application Ser. No. 08/045,585, filed April 9, 1993, now U.S. Pat. No. 5,693,521.

This invention was made with Government Support under Grant No. NS-27177, awarded by the National Institute of Health. The Government has certain rights in this invention.

BACKGROUND OF THE INVENTION

1. Field of the Invention

The present invention relates generally to biologically important phosphates such as second messengers. More particularly, the present invention relates to modifying second messengers to form derivatives which can be introduced into a cell without disrupting the cell membrane. Once inside the cell, the derivative is converted back to the biologically active second messenger.

2. Description of Related Art

The publications and other reference materials referred to herein to describe the background of the invention and to provide additional detail regarding its practice are hereby incorporated by reference. For convenience, the reference materials are numerically reference and grouped in the appended bibliography.

Second messengers are ions or small molecules that carry information from the cell membrane to targets on the inside of the cell. They play a major role in biological signal transduction and amplification (1). A common feature of most of the known second messengers, such as adenosine 3',5'-cyclic monophosphate (cAMP) (2,3), guanosine 3',5'-cyclic monophosphate (4) (cGMP), myo-inositol-1,4,5-triphosphate $(1,4,5)IP_3)$ or myo-inositol-1,3,4,5-tetrakisphosphate $(1,3,4,5)IP_4)$ (5), is the presence of phosphates. The correct number and position of these phosphates is essential for biological specificity and also confers extreme hydrophilicity (6,7).

The hydrophilicity of second messengers prevents endogenously generated molecules from leaking out of cells. As a result, high sensitivity is maintained within the responding cell and freedom from cross-talk between neighboring cells is achieved. However, the membrane impermeability of second messengers also makes deliberate extracellular application difficult or ineffective (2,6,8), even though such intervention would often be very useful for research or therapeutic reasons.

One approach for introducing phosphate containing compounds into cells involves using protective groups to reversibly convert the negatively charged phosphate compound into a neutral compound for transport through the cell membrane. The protective group is chosen so that it is enzymatically cleaved from the phosphate compound inside the cell to produce the original phosphate compound. For example, lipophilic, intracellularly hydrolyzable derivatives have been useful for amino, hydroxyl, and carboxylate moieties (9–12). Acetoxymethyl (AM) esters of polycarboxylate cation indicators and chelators are have also been used (12–14). Analogous acyloxyalkyl esters applied to phosphates are known, but they have been less widely exploited (15).

On simple model phosphates, uses of AM esters have been limited to potential therapeutic drugs, such as phosphonoformate (foscarnet) (16), antiviral nucleotides such as 5-fluoro-2'-deoxyuridine monophosphate (17,18), and a 3-phosphonate-containing inhibitor of the insulin receptor kinase (19). The phosphonoformate esters proved not to be biologically useful due to failure to hydrolyze to the correct products (16), but esterification was found to enhance the effectiveness of the antiviral nucleotides and kinase inhibitor (17–19).

Considerable work has been done on o-nitrobenzyl esters as photolyzable ("caged") derivatives of ATP (20), cyclic nucleotides (21,22), and inositol phosphates (23). However, the emphasis has been on producing a kinetically fast and complete transition from a monoester to the active freed phosphate metabolite (24,25), rather than as a general means of achieving membrane permeability. In addition, nitrobenzyl esters become cumbersome if more than one are required to mask negative charges, because multiple groups add considerable bulk and require high doses of UV to cause cleavage of all the groups.

Although numerous different myo-inositol polyphosphates are possible, only about a dozen have been found in cells. Their intracellular functions are controversial or unknown, except for myo-inositol 1,4,5-triphosphate $(IP_3)$, whose role as an intracellular second messenger to release $Ca^{2+}$ from internal stores is unquestioned (26). The next most studied inositol polyphosphate is myo-inositol 1,3,4,5-tetrakisphosphate $(IP_4)$, which is believed to cooperate with $IP_3$ to open $Ca^{2+}$-channels in the plasma membrane (27–30) or to resequester $Ca^{2+}$ released by $IP_3$ (31, 32). However, these hypotheses remain controversial (33–37).

Almost nothing is known about intracellular functions for other inositol polyphosphates. Detailed dissection of the roles of inositol polyphosphates is often difficult if they are endogenously generated in response to agonists, since such stimulation may affect multiple receptors, G proteins, diacylglycerol formation, multiple inositol polyphosphates, and yet other transduction pathways. Direct introduction of specific inositol polyphosphates is often preferable.

The high negative charge of inositol polyphosphates results in negligible passive permeability through membranes. Existing methods for introducing inositol phosphates include microinjection, patch-clamp techniques, and permeabilization by electroporation, detergents like saponin, or removal of extracellular $Ca^{2+}$. All these methods breach the plasma membrane and jeopardize the more complex functions and long-term viability of the cells. Furthermore, microinjection and patch techniques can only be applied to a few cells at a time.

In view of the above, there is a need to provide new compounds and procedures for increasing the membrane permeability of second messengers so that they can be introduced effectively into cells in amounts which are useful for investigational or therapeutic purposes.

SUMMARY OF THE INVENTION

In accordance with the present invention, compositions and methods are provided for increasing the permeability of phosphate-containing second messengers into a cell without disrupting the cell membrane. One aspect of the invention involves esterifying the phosphate groups present in the second messenger molecule to form an acyloxyalkyl ester derivative. The acyloxyalkyl ester of the second messenger has a neutral charge and therefor can permeate into the cell without disrupting the cell membrane. Once inside the cell, the esters are cleaved to convert the molecule back to its biologically active form. Acetoxymethyl esters worked well for cyclic nucleotide esters but proved insufficiently hydrophobic for inositol phosphates. Propionyloxymethyl and butyryloxymethyl esters are preferred for the latter class.

We discovered that esterification of the inositol phosphates with acetoxymethyl groups did not provide a sufficient increase in cell permeability to be useful. We discovered that more hydrophobic esters were required. Replacement of acetoxymethyl groups with propionyloxymethyl and butyryloxymethyl groups produces inositol phosphate esters which have much greater cell permeability rates while still being amenable to intracellular cleavage to form the active inositol phosphate. Inositol phosphates which have this high degree of cell permeability include those having the formula

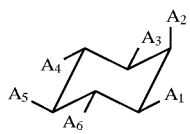

wherein $A_1$ to $A_6$ is H, OH, F or

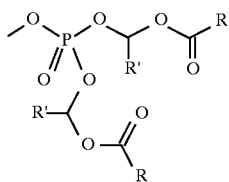

wherein R is an alkyl group having from 2 to 6 carbon atoms and R' is H or $CH_3$ or R is $CH_3$ and R' is $CH_3$ and wherein at least one of $A_1$ to $A_6$ is a phosphoester having the formula set forth above.

As a feature of the present invention, it was discovered that the release of active inositol polyphosphates within the cell can be accurately controlled by protecting or caging the 6-hydroxyl group of the inositol polyphosphate ester with a photolabile protecting group. Upon entry of the caged inositol polyphosphate ester into the cell, all of the protecting groups, except the caging group protecting the 6-hydroxyl group, are enzymatically removed. The resulting caged inositol polyphosphate remains in the cell in a inactive form until it is uncaged by exposure to ultraviolet light. This photoactivation feature allows one to accurately control the time when the active inositol polyphosphate is released within the cell.

The caged membrane-permeant second messengers include compounds which have the following formulas:

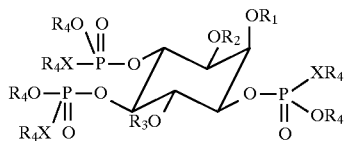

Wherein $R_1$ is H, —CHO, $COOCH_3$ or —$COCH_3$; $R_2$ is H or —$P(O)(OR_4)(XR_4)$; or $R_1$ and $R_2$ together are —$CH_2$—, —CHMe—, —$CMe_2$—, —CH(OMe)—, —CMe(OMe)— or —$C(OMe)_2$—; $R_3$ is a photolabile protecting group; $R_4$ is

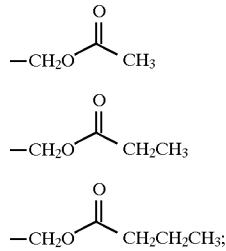

and
X is O or S.

The above described and many other features and attendant advantages of the present invention will become better understood by reference to the following description when taken in conjunction with the accompanying drawings.

BRIEF DESCRIPTION OF THE DRAWINGS

a. (1) $Bu_2SnO$, toluene, Dean-Stark apparatus, reflux, (2) DMNB-Br, CsF/DMF; b. S-(−)-camphanic acid chloride, TEA, DMAP; c. 2-mercaptoethanol, BF$_3$/Et$_2$O; d. BzCl, pyridine; e. 2-meraptoethanol, BF$_3$/Et$_2$O

a. K$_2$CO$_3$, MeOH/CH$_2$Cl$_2$; b. BzCl, pyridine, DMAP; c. 2-mercaptoethanol, BF$_3$/Et$_2$O; d. BzCl, pyridine, DMAP; e. 2-mercaptoethanol, BF$_3$/Et$_2$O; f. Trimethylorthoformate, BF$_3$/Et$_2$O, DMF; g. K$_2$CO$_3$, MeOH/CH$_2$Cl$_2$; h. (1) (CNCH$_2$CH$_2$O)$_2$PN(i-Pr)$_2$, tetrazole (2) t-BuOOH, CH$_2$Cl$_2$; i. NH$_4$OH, MeOH; j. PM-Br, DIEA/CH$_3$CN

DESCRIPTION OF THE PREFERRED EMBODIMENTS

Figure 1:
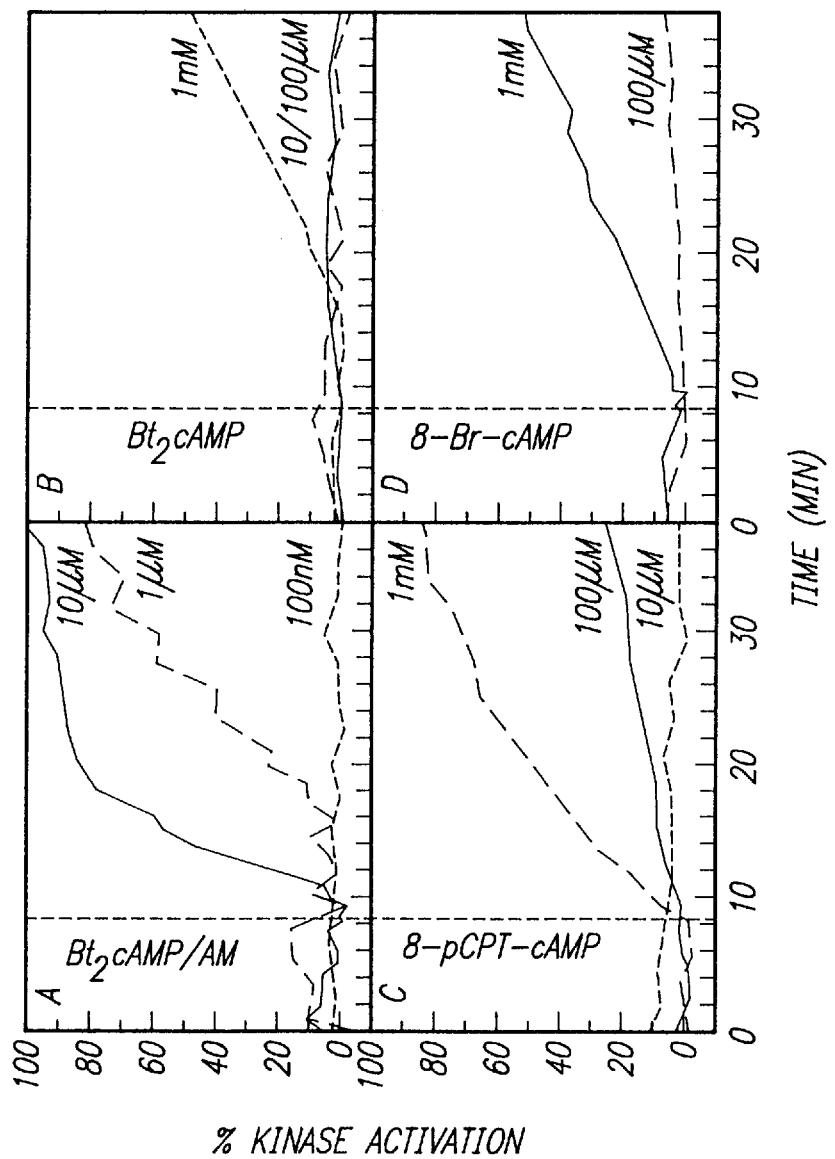
FIG. 1 is four graphic representations of the results of tests showing the kinase activation capability of $Bt_2cAMP/AM$ in comparison to other derivatives.

The present invention is directed to modifying second messengers and derivatives thereof which contain phosphates so that they can be easily introduced into a cell without disrupting the cell membrane. The invention involves esterifying the phosphate groups present in the second messenger to form a neutral acyloxyalkyl derivative which can readily diffuse through the cell membrane. The acyl group may contain up to 6 carbon atoms and is located at the 1 position of the alkyl group. The alkyl group may contain up to 7 carbon atoms. It was found for cAMP and cGMP that acetoxymethyl esters provide optimum cell membrane transport while still being amendable to cleavage from the second messenger after entry into the cell. Acetoxymethyl esters of inositol phosphates were found not to be optimally cell permeable. For second messengers having multiple phosphate groups, it is preferred that all of phosphate groups be masked as propionyloxymethyl or butyryloxymethyl esters.

The present invention is applicable to increasing the cell permeability of a wide variety of phosphate-containing second messengers and derivatives thereof. Preferred exemplary phosphate-containing second messengers include cAMP, cGMP, 1,4,5 IP$_3$, 1,3,4,5 IP$_4$ and myo-inositol 3,4,5,6-tetrakisphosphate. The present invention is also applicable to derivatives of cyclic nucleotides. Exemplary derivatives include the 8-substituted derivatives of cAMP or cGMP. The 8-substituted derivatives include 8-bromo-cAMP or cGMP, 8-chloro-cAMP or cGMP and 8-para-chlorophenylthio (cCPT) cAMP or cGMP.

It is preferred for cAMP and cGMP that the hydroxyl groups of the phosphate-containing second messengers be masked or protected during synthesis. Masking with acyl groups having up to 4 carbon atoms is preferred. Larger acyl groups are not preferred because they are more difficult for the cell to cleave from the second messenger.

Examples of practice showing the synthesis and use of cAMP/cGMP acetoxymethyl esters in accordance with the present invention are as follows:

Proton and $^{31}$P NMR spectra were obtained in CDCl$_3$, with residual CHCl$_3$ (δ=7.26), being used as the internal standard for $^1$H spectra. 85% phosphoric acid was used as an external standard for $^{31}$P spectra. All NMR spectra were recorded on either a Varian Gemini-200 (200 MHz) or a General Electric QE-300 (300 MHz) spectrometer and are reported with the following abbreviations: s, singlet; d, doublet; t, triplet; dd, doublet of doublets; m, complex multiplet. Fast atom bombardment mass spectroscopy (with glycerol as matrix) and precise mass determinations were performed by the mass spectroscopy facility of the University of California, Riverside. Capillary electrophoresis was performed on a Dionex CES.

Pyridine and acetonitrile used in the synthesis were stored over activated molecular sieve (3 Å) for at least 3 d. All other solvents were purchased in highest purity available and were used as received. N,N-Diisopropylethylamine (DIEA) was distilled from CaH$_2$. Acetoxymethyl bromide (AM-Br) was prepared according to known procedures (38). All nucleotides were from Sigma. Phenylphosphonic acid was from Fluka, Switzerland. 4-Methylumbelliferylphosphate was from Boehringer, FRG. All other reagents were from Aldrich.

TABLE 1

Structures of Acetoxymethyl Esters of Various Organic Phosphates

| comp. | structure | counter[a] ion M* | yield[b] | $^{31}$P-NMR [ppm] |
|---|---|---|---|---|
| 1 | 4-methylumbelliferyl phosphate bis(acetoxymethyl)ester | Ag* | 72% | −9.1 |
| 2 | phosphate tris(acetoxymethyl)ester | Ag* | 98% | −2.25 |
| 3 | phenylphosphonate bis(acetoxymethyl)ester | HDIEA* | 86% | 18.70 |
| 4a/4b | BlAde(BtGua) nucleoside cyclic phosphate AM ester | HDIEA* Ag* | 59% 52% | −8.0/[c] −5.0 |
| 5a/5b | | HDIEA* | 40% | −5.5/[c] −8.5 |

[a]M⁺ specifies the counter ion for the phosphate-containing starting material; HDIEA⁺ = diisopropylethylammonium.
[b]Yield by weight unless otherwise noted.
[c]Shift values for both diastereomers.

The compounds shown in Table 1 were synthesized as set forth below: Compounds 1–3 were synthesized for comparative purposes. Compounds 4a/b (cAMP/AM) and 5a/b (cGMP/AM) are preferred exemplary compounds in accordance with the present invention.

Synthesis of 4-Methylumbelliferyl Phosphate Bis (acetoxymethyl)ester (1)—The dilithium salt of 4-methylumbelliferyl phosphate (200 mg, 0.74 mmol) was dissolved in water and a concentrated solution of silver acetate was added. The disilver 4-methylumbelliferyl phosphate precipitated immediately and was filtered, washed with water and dried to a shining silver-white powder (yield: 277 mg, 79%). The silver salt (60 mg, 0.13 mmol) was suspended in 1 mL dry CH$_3$CN and 50 mg (0.33 mmol) AM-Br was added. At frequent intervals, the mixture was treated for 2 minutes at a time in an ultrasonic bath (Branson B-220). Frequent monitoring by $^1$H NMR showed the reaction to be complete after 4 hours. The supernatant was evaporated to dryness to yield 38 mg (72%) of 4-methylumbelliferyl phosphate bis(acetoxymethyl)ester (1); $^1$H NMR (CDCl$_3$, 200 MHz) δ 2.12 (s, 6H),;2.43 (s, 3H), 5.73 (dAB, 4H, J$_{AB}$=5.5 Hz, J$_{PH}$=14.2 Hz, —CH$_2$—), 6.27 (s, 1H, H3), 7.17–7.25 (m, 2H, H6,H8), 7.59 (m, 1H, H5); $^{31}$P NMR (CDCl$_3$, 121.5 MHz) δ-9.1; MS m/z (M+H)⁺ calcd 401.0638, obsd 401.0625.

Synthesis of Phosphate Tris(acetoxymethyl)ester (2)— Silver phosphate (30 mg, 71 μmol) was suspended in 0.5 mL dry CH$_3$CN and AM-Br (22 mg, 145 μmol) was added. After frequent sonication for 20 hours at room temperature, another 15 mg (100 μmol) AM-Br was added. When the suspended solid had lost its yellow color, the mixture was centrifuged (1000 rpm, 1 min), and the supernatant was evaporated to dryness and the residue was washed with dry toluene to give phosphate tris(acetoxy-methyl)ester (2) as a clear oil (yield 98%); $^1$H NMR (CDCl$_3$, 200 MHz) δ 2.15 (s, 9H), 6.45 (d, 6H, J$_{PH}$=13.5 Hz); $^{31}$P NMR (CDCl$_3$, 121.5 MHz) δ-2.25; MS m/z 241 (M-CH$_2$OAc)⁻.

Synthesis of Phenylphosphonate Bis(acetoxy-methyl) ester (3)—Phenylphosphonic acid (31.6 mg, 0.2 mmol) and diisopropylethylamine (DIEA, 130 mg, 1.0 mmol) were dissolved in 1 mL dry CH$_3$CN. AM-Br (77 mg, 0.5 mmol) was added and the solution was stirred at room temperature over night. After evaporation of the solvent the solid residue was extracted with dry toluene. Purification of the crude product 3 was performed on a Si60 column (10×40 mm) with 75% toluene/ 25% ethyl acetate to yield 52 mg 3 (86%) as a clear oil. $^1$H NMR (CDCl$_3$, 200 MHz) δ 1.95 (s, 6H), 5.66 (dAB, 4H, J$_{AB}$=5.3 Hz, J$_{PH}$=13.8 Hz, —CH$_2$—), 7.30–7.55 (m, 3H), 7.70 (m, 2H). $^{31}$P NMR (toluene-d$_8$, 121.5 MHz) δ 18.70.

Synthesis of N$^6$,O$^{2'}$-Dibutyryl Adenosine 3',5'-cyclic Monophosphate Acetoxymethyl Ester —bt$_2$cAMP/AM (4a/ 4b)—Two different methods were used to synthesize bt$_2$cAMP/AM. Method A: The sodium salt of N$^6$,O$^{2'}$-dibutyryl cAMP (12.5 mg, 25 μmol) was dissolved in 1 mL MeOH-H$_2$O (1:1) and passed through a Dowex 50W-X8 column (10×40 mm, H⁺-form). The free acid was eluted with 15 mL 50% MeOH. After evaporating to dryness, DIEA (6 mg, 50 μmol) and 1 mL dry CH$_3$CN were added. The reaction was started by the addition of AM-Br (16 mg, 94

μmol). After stirring the solution at room temperature for 4 days, the reaction mixture was chromatographed directly on a Si60 column (10×40 mm, 230–400 mesh) with 95% $CH_3CN$/5% hexane as the eluent under slight pressure. The eluant was collected in 5 mL fractions. Fractions 5–7 contained 5.3 mg (38% yield) of the faster eluting diastereomer of dibutyryl cAMP acetoxymethyl ester (4a) in high purity. $^1H$ NMR ($CDCl_3$, 300 MHz) δ 1.05 (t, 3H, J=7.0 Hz), 1.12 (t, 3H, J=7.0 Hz), 1.74 (m, 2H), 1.84 (m, 2H), 2.20 (s, 3H), 2.51 (m, 2H), 2.95 (t, 2H, J=7.0 Hz), 4.36 (ddd, 1H, J=2.7, 10.1, 10.1 Hz, H4'), 4.49 (dd, 1H, J=10.0, 10.0 Hz, $H5'_{ax}$), 4.66 (dddd, 1H, J=2.7, 10.0, 10.0, 22.1 Hz, $H5'_{eq}$), 5.67–5.95 (m, 4H, —$CH_2$—, H2', H3'), 6.04 (s, 1H, H1'), 8.01 (s, 1H, H2), 8.49 (broad s, 1H, $N^6H$), 8.78 (s, 1H, H8); $^{31}P$ NMR ($CDCl_3$, 121.5 MHz) δ-5.0 ppm.

Fractions 8+9 yielded 8.7 mg of a clear oil which contained diisopropyl-ethylammonium bromide and the slower eluting diastereomer of 4b (2:1 w/w as determined by NMR, yield 2.9 mg 4b, 21% from dibutyryl-cAMP). $^1H$ NMR ($CDCl_3$, 200 MHz), δ 0.99 (t, 3H, J=7.0 Hz), 1.05 (t, 3H, J=7.5 Hz), 1.70 (m, 4H), 2.18 (s, 3H), 2.45 (t, 2H, J=7.0 Hz), 2.89 (t, 2H, J=7.5 Hz), 4.40–4.70 (m, 3H, H4', $H5'_{eq}$, $H5'_{ax}$), 5.62–5.78 (AB-part of ABX, 2H, $J_{AB}$=5.1 Hz, —$CH_2$—), 5.83 (m, 2H, H2', H3'), 6.01 (s, 1H), 8.02 (broad s, 1H, H2), 8.51 (broad s, 1H, $N^6H$), 8.69 (s, 1H, H8); $^{31}P$ NMR ($CDCl_3$, 121.5 MHz) δ-8.0 ppm; MS (4a/4b 1:1 mixture) m/z $(M+H)^+$ calcd 542.1652, obsd 542.1681.

Method B: 58 mg (0.12 mmol) of the sodium salt of $Bt_2cAMP$ was dissolved in 0.5 mL $H_2O$ and 300 μL 1.8M $AgNO_3$ solution was added. The resulting white precipitate was filtered off washed with $H_2O$, and dried to yield 30.5 mg (45%, 54 μmol) of the silver salt of $Bt_2cAMP$. The white powder was suspended in 1 mL of dry $CH_3CN$ and 51 mg (330μmol) AM-Br were added. The suspension was frequently sonicated for 4h at room temperature. The two resulting diastereomeric acetoxymethyl esters 4a and 4b were purified as described under method A to yield 2.8 mg of the fast eluting isomer 4a (10% yield) and 9.6 mg (35%) of the slow eluting diastereomer 4b. NMR and MS analysis of the products of both methods were identical.

Synthesis of $N^2,O^{2'}$-Dibutyryl Guanosine 3',5'-cyclic Monophosphate Acetoxymethyl Ester $bt_2GMP$/AM (5at5b) —The sodium salt of $Bt_2cGMP$ (24 mg, 47 μmol) was passed through Dowex 50W-X8 ($H^+$ form) and the free acid was eluted with 15 mL 50% MeOH. After evaporating to dryness, 1 mL dry acetonitrile, 13 mg (100 μmol) DIEA and 21 mg (135 μmol) AM-Br were added. The solution was stirred overnight, evaporated to dryness, dissolved in $CH_3CN$/hexane (95:5, v/v) and eluted over a Si60 column (10×40 mm) to yield 11 mg (40%) of the two diastereomers of dibutyryl cGMP-AM (5a/5b) as a mixture. $^1H$-NMR (5a only, $CDCl_3$, 200 MHz) δ 1.00 (m, 6H), 1.74 (m, 4H), 2.38 (s, 3H), 2.42 (m, 2H), 2.48 (m, 2H), 4.18 (ddd,1H, J=4.0, 10.0, 10.0 Hz, H4'), 4.30–4.54 (m, 2H, $H5'_{ax}$, $H5'_{eq}$), 5.13 (ddd, 1H, J=1.8, 4.1, 10.0 Hz, H3'), 5.56 (dd, 1H, J=4.1, 4.1 Hz, H2'), 5.71 (dAB, 2H, J=12.5, 9.1 Hz, —$CH_2$—), 6.04 (d, 1H, J=4.0 Hz, H1'), 7.65 (broad s, 1H, $N^2H$), 10.14 (s, 1H, H8), 12.30 (broad s, 1H, $N^1H$); $^{31}P$ NMR ($CDCl_3$, 121.5 MHz) δ-5.5 and -8.5 ppm; MS m/z $(M+H)^+$ calcd 558.1601, obsd 558.1611.

The most general and economical synthetic route to acetoxymethyl phosphate esters is believed to be alkylation of the parent phosphate anions by acetoxymethyl halides. The instability of acetoxymethanol precludes its phosphorylation. Preliminary synthetic attempts, similar to the experiments of Srivasta and Farquhar (15), were performed on 4-methylumbelliferyl phosphate and phenyl phosphonate as readily available model compounds detectable by UV absorption and bearing no competing nucleophilic centers. 4-Methylumbelliferyl phosphate bis(acetoxymethyl)ester (Table I-1) was successfully prepared in 73% yield by suspending the disilver salt of 4-methylumbelliferyl phosphate in dry acetonitrile, adding acetoxymethyl bromide (AM-Br) (38), and sonicating the heterogeneous mixture at frequent intervals for 24 hours. The $^1H$ NMR of the supernatant showed an AB doublet at 5.7 ppm for the methylene group of the acetoxymethyl ester, a typical pattern for all phosphate acetoxymethyl esters reported here. The synthesis of phosphate tris(acetoxymethyl)ester (Table I-2) offered a possibility to directly monitor the progress of the reaction. Yellow $Ag_3PO_4$ was reacted with AM-Br as described above. Disappearance of the color after 36 hours indicated completion of the reaction. The product was the only compound in the organic phase (98% yield).

An alternative to silver salts is desirable for polyphosphates or molecules bearing oxidizable functionalities. Direct treatment of phenylphosphonic acid with an excess of the hindered base diisopropylethylamine (DIEA) and AM-Br eventually gave an 86% yield of the phenylphosphonate bis(acetoxy-methyl)ester (Table I-3).

Analogous reactions worked, albeit in lower yield, for $N^6,2'$-O-dibutyryl adenosine 3',5'-cyclic monophosphate acetoxymethyl ester ($Bt_2cAMP$/AM,4a/4b) and $N^2,2'$-O-dibutyryl guanosine 3',5'-cyclic monophosphate acetoxymethyl ester ($Bt_2cGMP$/AM, 5a/5b). The commercially available sodium salts of $Bt_2cAMP$ and $Bt_2cGMP$ were converted into the free acids on Dowex 50W-X8 and then into DIEA salts. Reaction took place in dry $CH_3CN$ with an excess of DIEA and AM-Br for 5 days at room temperature. Both nucleotide AM-esters were purified on silica gel 60 ($CH_3CN$/hexane 19:1 v/v) after evaporation of the solvent. The two diastereomers of $Bt_2cAMP$/AM (4a/4b) were isolated in yields of 37% and 21% for the fast and slow-eluting isomers, the latter co-eluting with residual DIEA. $^{31}P$-NMR resonances were -5.0 ppm and -8.0 ppm, respectively, but absolute configurations were not determined. The analogous two diastereomers of $Bt_2cGMP$/AM (5a/5b) could not be separated under the described conditions, but were free of DIEA. $Bt_2cAMP$/AM was also prepared by alkylating the silver salt of $Bt_2cAMP$ with AM-Br in $CH_3CN$ with frequent sonication for 24 h. These heterogeneous conditions reversed the enantiomeric preference, giving the fast and slow-migrating isomers in 10% and 35% yields.

Figure 8:
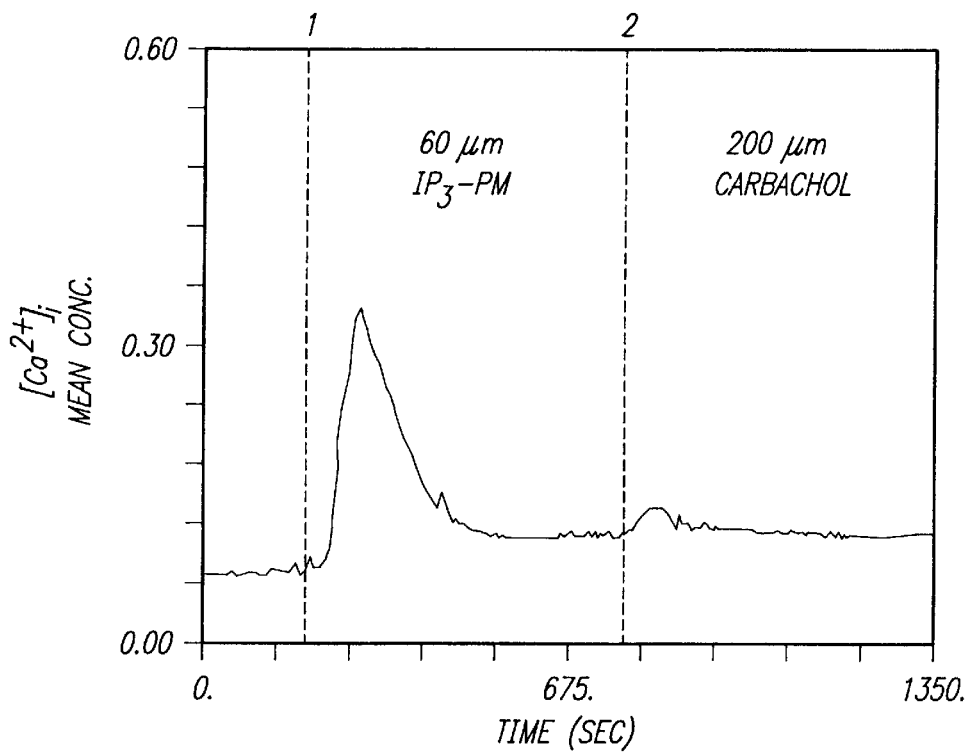
FIG. 8 depicts test results showing permeation of $IP_3/PM$ at a dose of 60 μm into astrocytoma cells in a medium lacking extracellular $Ca_{2+}$.

The synthesis of cAMP and cGMP described above utilizes butyryl groups to mask or protect the hydroxyl groups. This is because the direct conversion of a cAMP or cGMP into their acetoxy esters yields only minute amounts of product. Trimethylsilyl (TMS) groups were also found to work well as a protective group. The synthesis schemes for direct and TMS protected synthesis is shown in FIG. 8.

Synthesis of the acetoxy ester of cAMP using TMS is set forth below:

General Methods—Proton and $^{31}P$ NMR spectra were obtained in $CDCl_3$ with residual $CHCl_3$ (δ=7.26), being used as the internal standard for $^1H$ spectra. 85% phosphoric acid was used as an external standard for $^{31}P$ spectra. All NMR spectra were recorded on either a Varian Gemini-200 (200 MHz) or a General Electric QE-300 (300 MHz) spectrometer and are reported with the same abbreviations as in the preceding examples.

Acetonitrile were stored over activated molecular sieve (3 Å) for at least 3d. All other solvents were purchased in highest purity available and were used as received. N,N-

Diisopropylethylamine (DIEA) was distilled from $CaH_2$. Acetoxymethyl bromide (AM-Br) was prepared according to known procedures. cGMP was from ICN or Calbiochem. All other nucleotides were from Sigma. All other reagents were from Aldrich.

Figure 4:
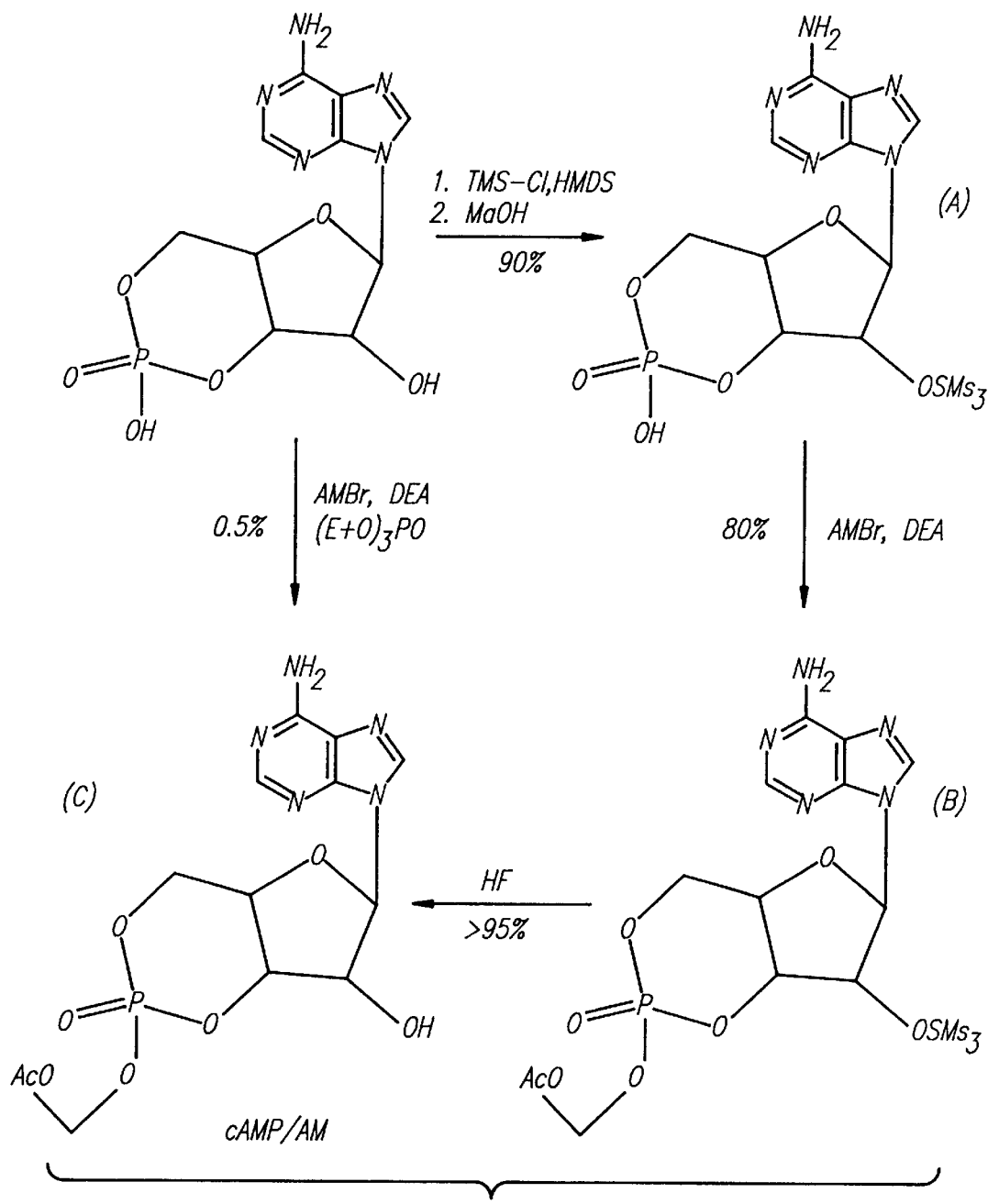
FIG. 4 depicts the synthesis scheme preparing 3',5'-cyclic monophosphate acetoxymethyl ester.

The following three step synthesis is outlined in FIG. 4.

Synthesis of 2'-O-Trimethylsilyl Adenosine 3',5'-cyclic Phosohate (FIG. 4A)—The free acid of cAMP (50 mg, 0.15 mmol) was suspended in 3 mL dry DIEA. One (1) mL Hexamethyidisilazane (HMDS) and 0.5 mL Trimethylsilyl chloride (TMS-CI) were added under Ar and the mixture was heated to 100° C. for 3 hours. After cooling to r.t. all volatile components were evaporated off in high vacuum. The residual oil was extracted with 2×2 mL dry toluene. A sample of the extract, exclusively containing $N^6,2'$-O-di (trimethylsilyl) adenosine 3',5'-cyclic monophosphate trimethylsilyl ester, was evaporated to dryness and analyzed by NMR: $^1H$ NMR (toluene-dg, 200 MHz) diastereomer 1 (80%) δ 0.32 (s, 9H), 0.45 (s, 9H), 0.47 (s, 9H), 4.15–4.61 (m, 3H, H4', $H5'_{eq}$, $H5'_{ax}$), 4,98 (d, 1H, J=4.7 Hz, H2'), 5.60 (s, 1H, $N^6H$), 5.74 (ddd, 1H, J=1.6, 4.7, 9.5 Hz, H3'), 5,83 s, 1H, H1', 7.64 (s, 1H, H2), 8.6 (s, 1H, H8). Diastereomer 2 (20%) δ 4.65 (d, 1H, J=4.2 Hz, H2'), 5.20 (m, 1H, H3'), 5.66 (s, 1H, $N^6H$); 6.05 (s, 1H, H1'), 7.77 (s, 1H, H2), 8.58 (s, 1H, H8). The toluene extract was treated with 12 µL MeOH (0.3 mmol) for 3 min. followed by rapid evaporation of the solvents. The remaining white solid fairly pure 2'-O-TMS-cAMP (1). $^1H$ NMR (CD, OD, 200 MHz) δ 0.80 (s, 9H, TMS), 4.32 (m, 3H, H4', H5'), 4.65 (d, 1H, J=8.2 Hz, H2'), 4.95 (m, 1H H3'), 6.12 (s, 1H, H1'), 7.16 (broad s, 2H, $NH_2$), 8.40, 8.45 (2s, 1H each, H2, H8). $^{31}$H-NMR O.

Synthesis of 2'-O-Trimethylsilyl Adenosine 3',5'-cyclic Monophosphate Acetoxymethyl Ester (FIG. 4-B)—25 mg (0.062 mmol) 2'-TMS-cAMP (1) was dissolved in 0.5 mL dry $CH_3CN$ containing 0.05 mL DIEA (0.28 mmol) under Ar and 0.028 mL (0.28 mmol) AMBr were added. The mixture was stirred for 3 days at r.t. then evaporated to dryness. The crude produce was purified on a Si60 column (4×1.5 cm) with dry $CH_3CN$ saturated with hexane as the eluent. Prior to the separation the column was washed with the same eluent containing 0.1% acetic acid followed by the eluent alone. Most of the 2'-O-TMS-cAMP/AM (2) eluated just before $HDIEA^+Br$ to yield 20.5 mg (0.042 mmol, 68%). The product consisted of 90% of one of the $R_P/S_P$-diastereomers, as determined by $^{31}P$ NMR. $^1H$ NMR ($CDCl_3$, 300 MHz) δ 0.22 (s, 9H, TMS), 2.16 (s, 3H, —$OCCH_3$), 4.43 (m, 2H, H4', $H5'_{ax}$), 4.64 (m, 1H, $H5'_{eq}$), 4.85 (d, 1H, J=5.2 Hz, H2'), 5.34 (m, 1H, H3'), 5.74 (d, 2H, J=13.1 Hz, —$CH_2$—OAc), 4.86 (broad s, 2H, $NH_2$), 5.91 (s, 1H, H1'), 7.87 and 8.41 (2s, 1H each, H2 and H8). $^{31}P$ NMR ($CDCl_3$, 121.5 Hz) δ-7.58 (90%), -4.62 (10%).

Synthesis of Adenosine 3',5'-cyclic Monophosphate Acetoxymethyl Ester (FIG. 4-C)—14 mg (0.029 mmol) of 2 were dissolved in 1 mL of a 1:1 (v/vO mixture of CHCl3/ $CH_3CN$ and 2 µL HF (49%) was added. The mixture was gently swirled for 2 min. before the solvents were evaporated off to quantitatively yield cAMP/AM (3) as a white solid. $^1H$ NMR ($CD_3OD$, 300 MHz) δ 2.17 (s, 3H, —OAc), 4.48 (ddd, 1H, J=3.6, 9.5, 9.5 Hz, H4'), 4.50 (m, 1H, $H5'_{ax}$), 4.74 (m, 1H, $H5'_{eq}$), 5.33 (ddd, 1H, J=1.0, 4.8, 12.3 Hz, H3'), 5.75 (m, 2H, —$CH_2$—OAc), 6.15 (s, 1H, H1'), 8.41 and 8.42 (2s, 1H each, H2, H8). $^{31}P$ NMR ($CD_3OD$, 121.5 MHz) δ-6.85.

The following biological tests were conducted to demonstrate the biological activity of the cAMP derivative after it passes into the cell.

Activation of intracellular protein kinase A. The premier target of cAMP in most cells is the cAMP-dependent protein kinase (PKA) (45). To show that this enzyme can be activated by extracellular application of $Bt_2cAMP/AM$, we used a recently-developed assay for PKA activation in single cells (39). When PKA is doubly labeled with fluorescein on its catalytic subunits and rhodamine on its regulatory subunits to produce FICRhR, fluorescence energy transfer from the fluorescein to rhodamine occurs in the holoenzyme complex but is disrupted upon activation and dissociation of the subunits. The change in the ratio of fluorescein to rhodamine emissions parallels the increase in kinase activity and can be nondestructively imaged in single cells. REF-52 fibroblasts were microinjected with FICRhR and emission ratio images recorded at room temperature as previously described (27). 30 min after injection, 0.1, 1, or 10 µM $Bt_2cAMP/AM$ were added extracellularly (FIG. 1-Graph A). The highest dose yielded a maximal change in fluorescence ratio within 15 min. The intermediate dose gave a shallower slope and a lower plateau to slightly over 50% of the maximal change. The onset of the separation of regulatory and catalytic subunit of FICRhR occurred roughly 2 min after the addition of the cAMP derivative. Much the same delay and overall time course occurred with nonesterified $Bt_2cAMP$, though much higher concentrations, 1 mM, were required (FIG. 1-Graph B). Other widely used, supposedly lipophilic CAMP derivatives showed no delay in beginning to activate PKA, but millimolar concentrations were still required (FIG. 1-Graphs C & D).

To show that intracellular enzymatic hydrolysis of the ester groups is required we examined the binding properties of $Bt_2cAMP/AM$ and $Bt_2cAMP$ to FICRhR in vitro. The highest concentration of $Bt_2cAMP/AM$ used in the other assays (10 µM) gave no separation of the subunits, while $Bt_2cAMP$ was roughly 1/100 as potent as cAMP probably due to contamination by 1% monobutyryl-cAMP as specified by the supplier (Sigma) (See Table II).

TABLE II

| In-vitro cAMP-dependent kinase activation assay. | | | | | |
|---|---|---|---|---|---|
| | cAMP | | $Bt_2cAMP^a$ | | $Bt_2cAMP/AM$ |
| concentration [µM] | 1 | 10 | $200^b$ | 10 | 10 | 10 |
| % kinase$^c$ activation | 67 | 91 | 100 | 16 | 61 | 0 |

$^a$The slight residual activity of $Bt_2cAMP$ is probably due to an impurity of $N^6$-monobutyryl cAMP (1%) as specified by the supplier.
$^b$200 µM cAMP was considered the maximal dose necessary to fully dissociate FICRhR.
$^c$Labelled cAMP-dependent kinase type I (FICRhR). This labelled isoform is more stable against subunit dissociation in the absence of cAMP at the low enzyme concentrations used in this assay than labelled type II.

Figure 2A:
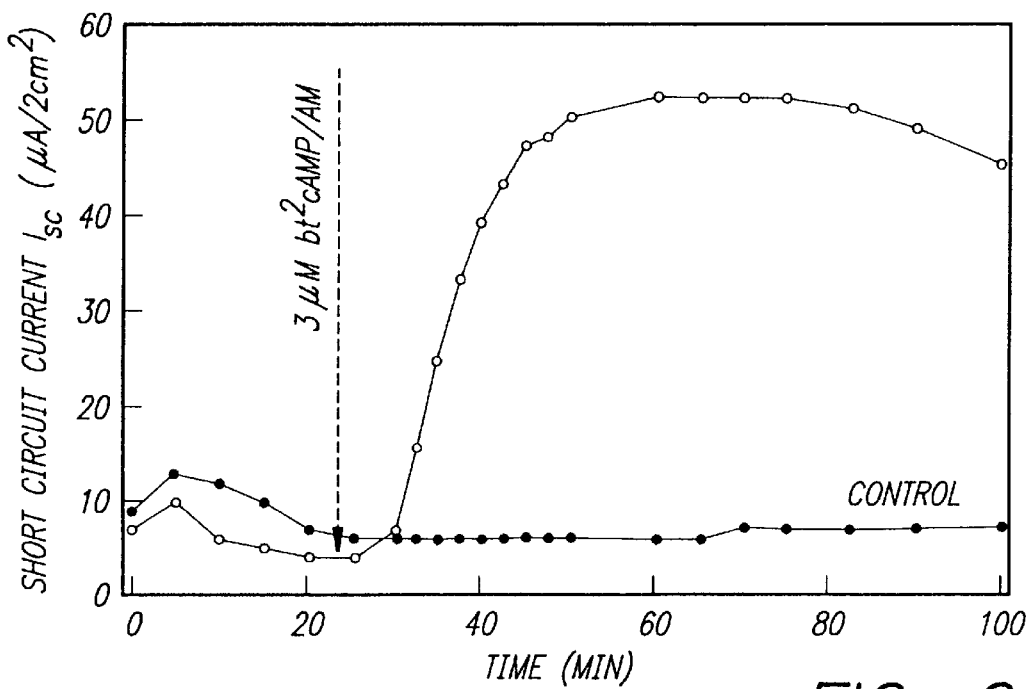
FIG. 2A is a graphic representation of the results of tests showing the initiation of $Cl^-$ secretion by $Bt_2cAMP/AM$.
Figure 2B:
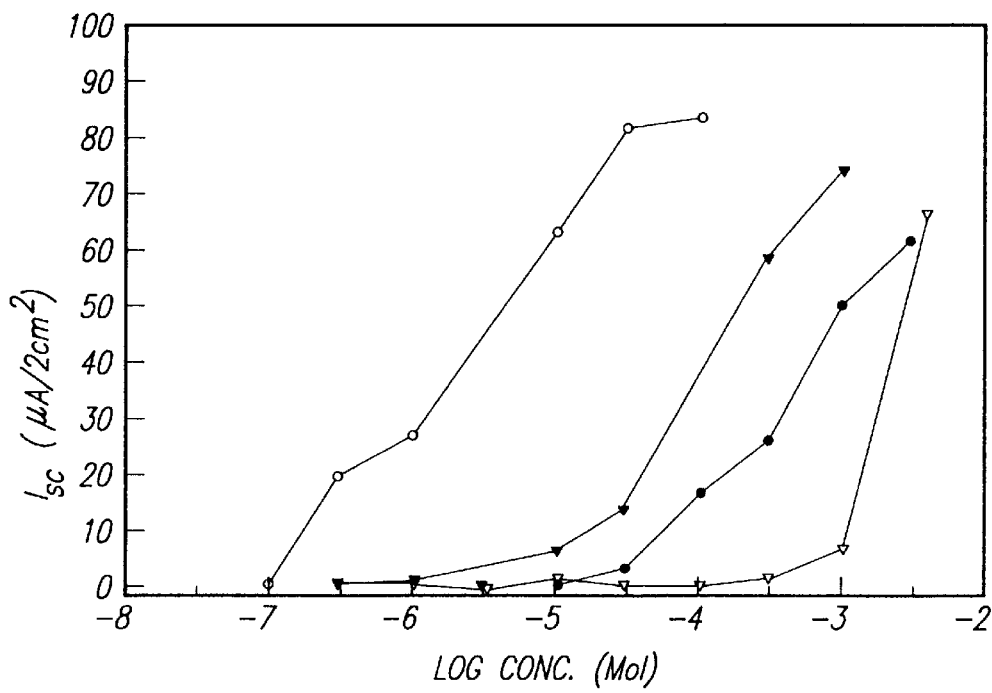
FIG. 2B is a graph showing a comparison of chloride secretion initiated by $Bt_2cAMP/AM$ and other derivatives.

One of the many well-known cell functions controlled by cAMP is intestinal transepithelial $Cl^-$-secretion (46). A convenient test system is the intestinal cell line $T_{84}$, in which chloride secretion can be continuously monitored by mounting confluent monolayers of cells in Ussing chambers (42). FIG. 2A shows the $Cl^-$-secretion measured as short circuit current ($I_{SC}$) across the cells. The addition of $Bt_2cAMP/AM$ at a concentration of 3 µM to the serosal bathing solution caused an increase in $I_{SC}$ with a maximum after 20 min. Higher concentrations of the derivative caused faster but not significantly greater responses, whereas lower concentrations reached lower maximum $I_{SC}$ values. The $I_{SC}$ values obtained at an arbitrary intermediate time, 12 min after addition of various cAMP-derivatives, were used to determine the dose dependency (FIG. 2B). The dose response curves were parallel, with $EC_{50}$ values of 2 µM and 400 µM for Bt$_2$cAMP/AM and Bt$_2$cAMP respectively. Therefore the introduction of the acetoxymethyl group on the phosphate increased the potency by 200 fold in this assay by circumventing the permeability barrier. Furthermore, the acetoxymethyl ester seems to be cleaved inside T$_{84}$ cells without significant delay, since the two agents gave essentially indistinguishable kinetics of activation. Tests with the cAMP-derivatives 8-Br-cAMP and 8-pCPT-cAMP showed activation of Cl$^-$-secretion with EC$_{50}$ values of 1.5 mM and 100 μM, respectively.

Figure 3A:
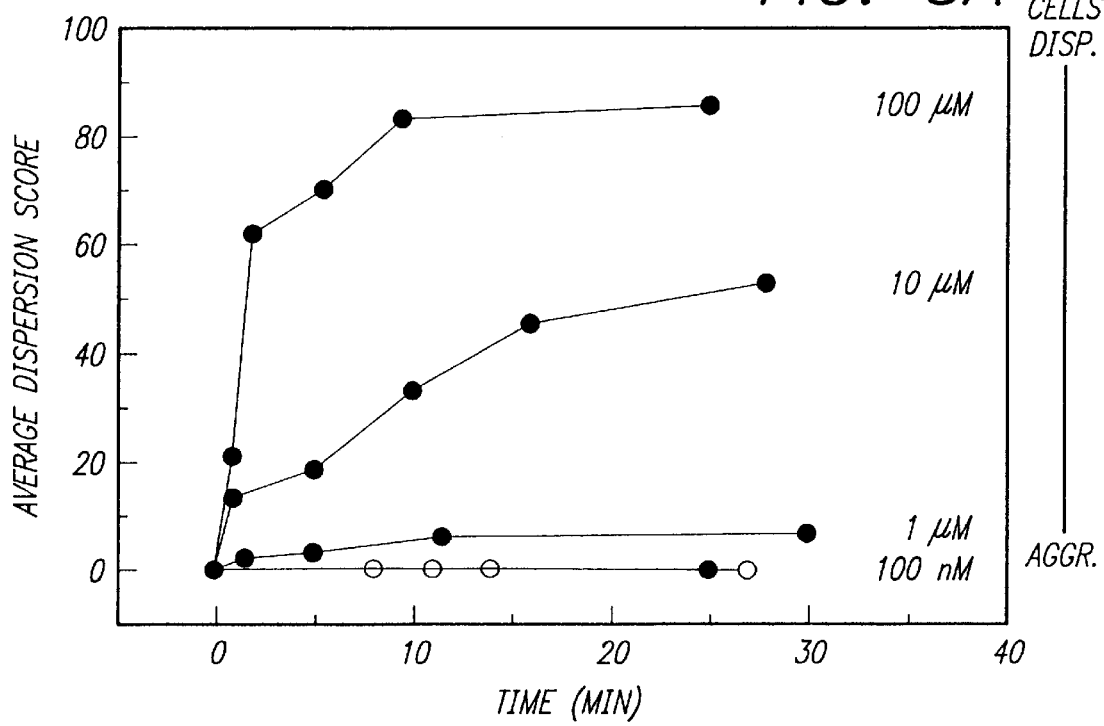
FIG. 3A shows the results of tests demonstrating the ability of $Bt_2cAMP/AM$ to disperse fish dermal chromatophores.
Figure 3B:
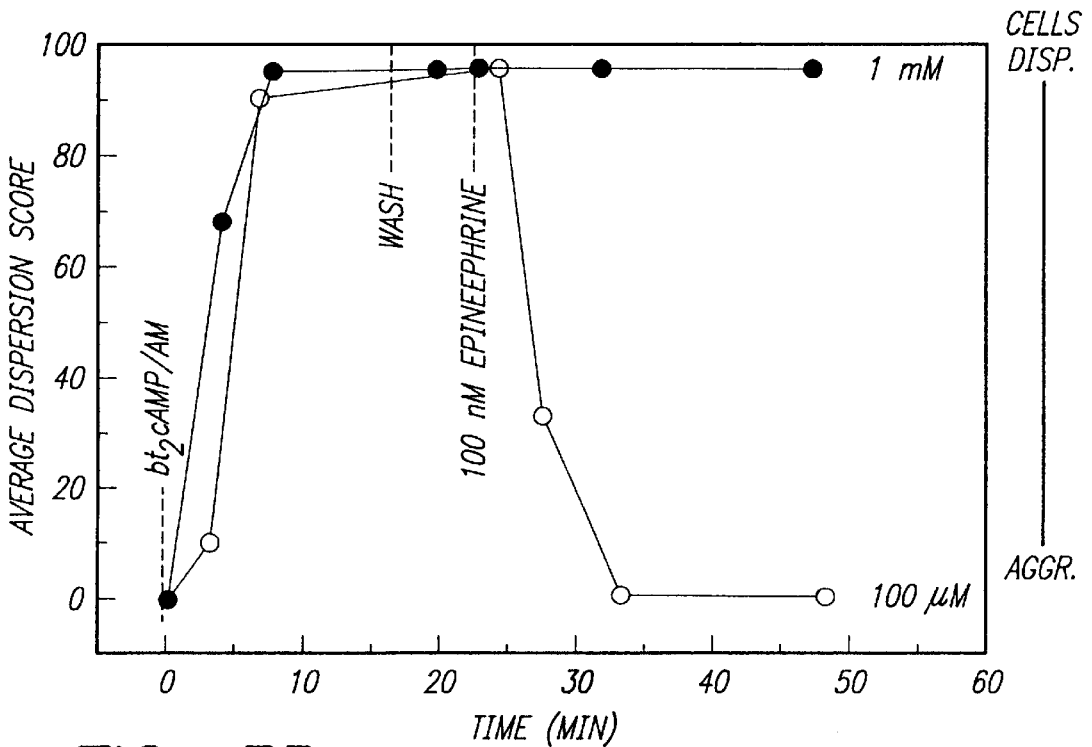
FIG. 3B is a graph showing test results demonstrating the reversibility of the dispersion shown in FIG. 3A.

Fish dermal chromatophores exhibit a tightly regulated movement of pigment granules either inward into a highly aggregated central mass, or outward, dispersing the pigment throughout the cell. In angelfish (*Pterophyllum scalare*) melanophores this movement is microtubule based and cAMP regulated (44,47) but relatively refractory to external cAMP analogs. Melanophores permit a visual single-cell assay for the ability of cAMP analogs to enter cells and mimic cAMP actions. The melanophores were isolated on angelfish scales and the epidermis was stripped off. The 60–100 melanophores per scale were pretreated with an α$_2$-adrenergic agonist to reduce endogenous cAMP and start with full aggregation. Extracellular Bt$_2$cAMP/AM then caused dispersion of the pigment in a dose-dependent manner (FIG. 3A). A concentration of 100 μM Bt$_2$cAMP/AM was enough to cause essentially complete dispersal; however, 1 mM gave a slightly faster onset of action and could not be readily reversed by removal of the extracellular Bt$_2$cAMP/AM and administration of epinephrine, whereas the effect of 100 μM was easily reversed (FIG. 3B). Dispersion was just detectable at 1 μM and half-maximal near 10 μM (FIG. 3A). By comparison, 1 mM Bt$_2$cAMP was unable to cause any detectable dispersion. Hence the AM ester group increased the potency by more than 1000 in this assay. The effectiveness of Bt$_2$cAMP/AM shows that the inertness of Bt$_2$cAMP in melanophores is due to poor permeability rather than susceptibility of Bt-cAMP to phosphodiesterases or selectivity of a kinase binding sites for cAMP substitution (48). The preceding examples are summarized in (64).

The preceding strategy for increasing permeability of cAMP and cGMP, i.e. acetoxymethyl esterification in combination with butyryl group masking of the hydroxyl groups, was found not to be effective for inositol phosphates. Acetoxymethyl esters of inositol triphosphates which had their hydroxy groups blocked with butyryl groups were found, to have relatively low potency, perhaps because butyryl esters located between bulky phosphate groups cannot be cleaved by intracellular enzymes. However, if the hydroxyl groups were left unesterified and the phosphates were esterified with acetoxymethyl groups, the resulting compounds had insufficient membrane permeability to enter cells. We found that, in addition to leaving the hydroxyl groups unesterified, it was also necessary to replace the acetoxymethyl groups with more hydrophobic groups in order to provide acceptable cell permeability and subsequent ester cleavage. We discovered that more hydrophobic esters such as, propionyloxymethyl(PM) esters (R=ethyl, R'=H) or butyryloxymethyl(BM) esters (R=propyl, R'=H), permeate the cell membrane at higher rates while still being amenable to cleavage upon entry into the cell.

Inositol phosphate esters in accordance with the present invention have the formula

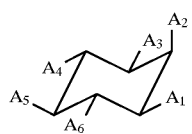

wherein A$_1$ to A$_6$ is H, OH, F or

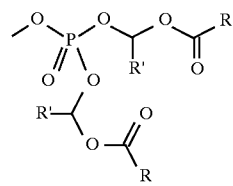

wherein R is an alkyl group having from 2 to 6 carbon atoms and R' is H or CH$_3$ or R is CH$_3$ and R' is CH$_3$ and wherein at least one of A$_1$ to A$_6$ is a phosphoester having the formula set forth above.

Preferred esters are the propionyloxymethyl and butyryloxymethyl esters of: inositol-1,4,5-triphosphate; 3-deoxy-inositol-1,4,5-triphosphate; 3-fluoro-inositol-1,4,5-triphosphate; inositol-1,3,4-triphosphate; inositol-1,3,4,5-tetraphosphate; and inositol-3,4,5,6-tetraphosphate.

Figure 5:
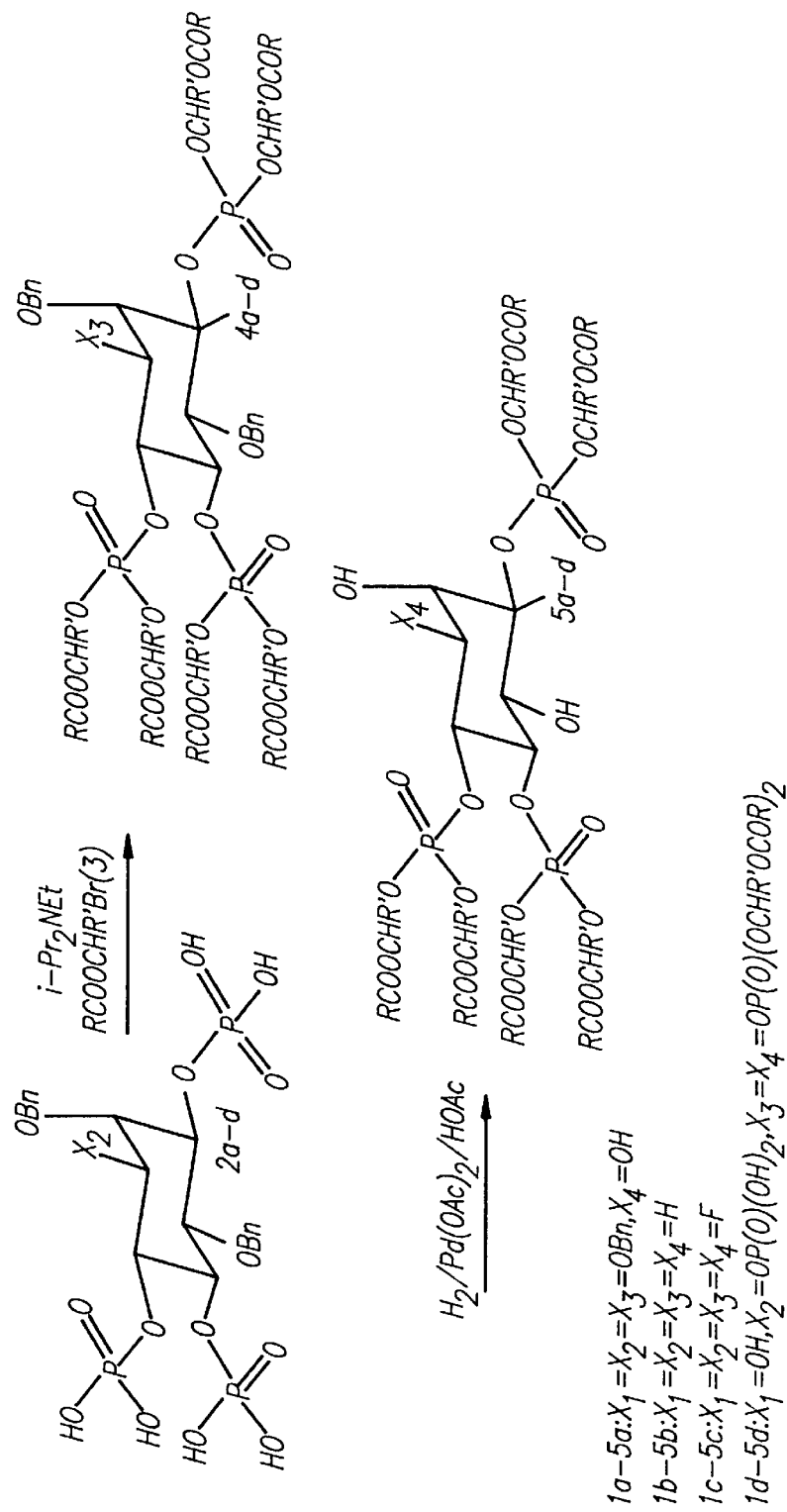
FIG. 5 is a schematic representation of the synthesis of exemplary esters of inositol phosphates.

Examples of synthesis and use of preferred exemplary inositol polyphosphate esters in accordance with the present invention is as follows:

The general synthesis scheme which may be used to make a number of different esters in accordance with the present invention is set forth in FIG. 5.

The synthesis of phosphotriesters with neighboring unprotected hydroxyls is difficult because the phosphates very easily migrate or cyclize into the free hydroxyls. The key is to use benzyl ethers to protect the hydroxyls for as many steps as possible and to find conditions to remove the benzyls at the last stage without affecting the phosphate acyloxyalkyl esters (FIG. 5). Thus in the synthesis of, for example, inositol triphosphate propionyloxymethyl ester (IP$_3$/PM), the hydroxyls on the 2, 3, and 6-positions are initially protected as benzyl groups. Phosphorylation of 1 with bis(β-cyanoethyl)N,N-diisopropylphosphoramidite, oxidation of the phosphites, and ammonolysis of the cyanoethyl protecting groups affords 2,3,6-tri-O-benzyl-IP$_3$ (2a). Esterification with bromomethyl propionate (3, R=Et, R'=H) gives fully protected inositol trisphosphate (4a). Finally, catalytic hydrogenolysis over palladium acetate in acetic acid provides IP$_3$/PM (5a, R=Et, R'=H) without phosphate migration or cyclization. This general procedure may be used to synthesize other membrane-permeant, intracellularly hydrolyzable esters of IP$_3$ and other important inositol polyphosphates such as 3-deoxy-1,4,5-IP$_3$, 3-fluoro-1,4,5-IP$_3$, 1,3,4-IP$_3$, 1,3,4,5-IP$_4$, and 3,4,5,6-IP$_4$.

A detailed description of the synthesis is as follows:

D-2,3,6-tri-O-benzyl-myo-inositol 1a and D-2,6-di-O-benzyl-myo-inositol 1d, which are known compounds (65, 66), are synthesized from myo-inositol by a modified procedure (for 1a) or as published (for 1d). D-2,3-di-O-benzyl-3-deoxy-myo-inositol 1b and D-2,3-di-O-benzyl-3-deoxy-3-fluoro-myo-inositol 1c, may be prepared in two steps from known precursors (67,68), D-1,4,5-tri-O-benzoyl-6-O-benzyl-3-deoxy-myo-inositol (compound 10 in ref. 67) or D-1,4,5-tri-O-benzoyl-6-O-benzyl-3-deoxy-3-fluoro-myo-inositol (compound 5b in ref. 68) respectively. These starting materials may be benzylated with benzyl trichloroacetimidate in the presence of a catalytic amount of trifluoromethanesulfonic acid. Removal of the benzoyl protecting groups with potassium carbonate in methanol overnight affords 1b and 1c, respectively. The experimental procedure outlined in FIG. 5 is similar for 5a, 5b, 5c and 5d. Here we use 5a as an example. All reactions are done under an atmosphere of argon unless otherwise specified.

D-2,3,6-tri-O-benzyl-myo-inositol-1,4,5-triphosphate (2a), ammonium salt: 65 mg 1a (0.144 mmol) was dissolved in 1 ml dichloromethane and 1 ml acetonitrile. Bis(β-cyanoethyl)-N,N-diisopropylphosphoramidite (69)(180 μl, 0.65mmol) was added, followed by 48 mg tetrazole (0.69 mmol) dissolved in 1.2 ml acetonitrile. After stirring at room temperature for 2 hours, the reaction flask was cooled in an ice bath. An excess of t-butyl hydroperoxide (300 μl of a 5M solution in dichloromethane) was added in one portion. Thirty minutes later, the ice bath was removed and stirring was continued at room temperature for another hour. The solvent was removed under reduced pressure. The remaining syrup was resuspended in the minimum amount of dichloromethane/methanol (12:1). 130 mg of a clear glass was obtained. This material was dissolved in 1.5 ml methanol and mixed with 6 ml concentrated ammonium hydroxide. It was refluxed at 60° C. for 3 hours and the solvent was removed under reduced pressure. The remaining material was used directly for the next step without further purification.

D-2,3,6-tri-O-benzyl-myo-inositol-1,4,5-triphosphate propionyloxymethyl ester (4a). The above material (2a) was suspended in 1 ml acetonitrile and 0.2 ml diisopropylethylamine (DIEA). It was then sonicated for a short interval and the solvent was removed under reduced pressure. This process was repeated a few more times until a homogeneous solution was obtained after adding acetonitrile and DIEA, indicating that the counterions for the phosphate groups had been exchanged from ammonium to diisopropylethylammonium. An excess (~150 μl) of bromomethyl propionate (3, R=Et, R'=H, prepared as in ref. 70) was then added and left to react for 48 hours. The solvent was removed under vacuum and the remaining syrup was first purified by silica gel flash column chromatography, eluting with ethyl acetate. The pale yellow glass obtained upon evaporation was further purified by HPLC on a C18 reverse-phase column, eluting with 78% methanol in water. 15 mg clear glass was obtained, 10% overall yield from 1a. $^1$H-NMR (CDCl$_3$): δ=1.1 (m, 18H), 2.2–2.45 (m, 12H), 3.5 (dd, 1H, J=12 Hz, 2 Hz), 4.05 (t, 1H, J=11.2 Hz), 4.3–4.5 (m, 3H), 4.7–4.9 (m, 7H), 5.3–5.7 (m, 12H), 7.2–7.5 (m, 15H), FAB MS m/z (M+Cs)$^+$. Calculated: 1339.2293. Observed: 1339.2261.

D-myo-inositol-1,4,5-triphosphate propionyloxymethyl ester (5a, R=Et, R'=H). 15 mg 4a was dissolved in 2 ml glacial acetic acid. 20 mg palladium acetate and a catalytic amount of trifluoroacetic acid was added. The mixture was stirred under 1 atm hydrogen gas at a temperature below 20° C. to minimize phosphate triester migration. After 4 hours of hydrogenation, the catalyst was filtered off and the acetic acid was lyophilized. 10 mg clear glass was obtained. $^1$H-NMR (CD3OD): δ=1.2 (m, 18H), 2.4 (m, 12H), 3.7 (dd, 1H, J=9.9 Hz), 2.4 Hz), 4.0 (t, 1H, J=9.3 Hz), 4.2–4.4 (m, 3H), 4.65 (q, 1H, J=8.4Hz), 5.7 (m, 12H).

D-myo-inositol-1,4,5-triphosphate butyryloxymethyl ester (5a, R=Pr, R'=H) was prepared identically but with bromomethyl butyrate (3, R=Pr, R'=H) in place of bromomethyl propionate. $^1$H-NMR (CD3OD): δ=0.95 (m, 18H), 1.7 (m, 12H), 2.4 (m, 12H), 3.7 (dd, 1H, J=9.9 Hz, 2.4 Hz), 4.0 (t, 1H, J=9.3 Hz), 4.2–4.4 (m, 3H), 4.65 (q, 1H, J=8.4Hz), 5.7 (m, 12H). FAB MS m/z (M+Cs)$^+$. Calculated: 1153.1824. Observed: 1153.1850.

Biological Applications of IP$_3$/PM and IP$_3$/BM

Figure 6:
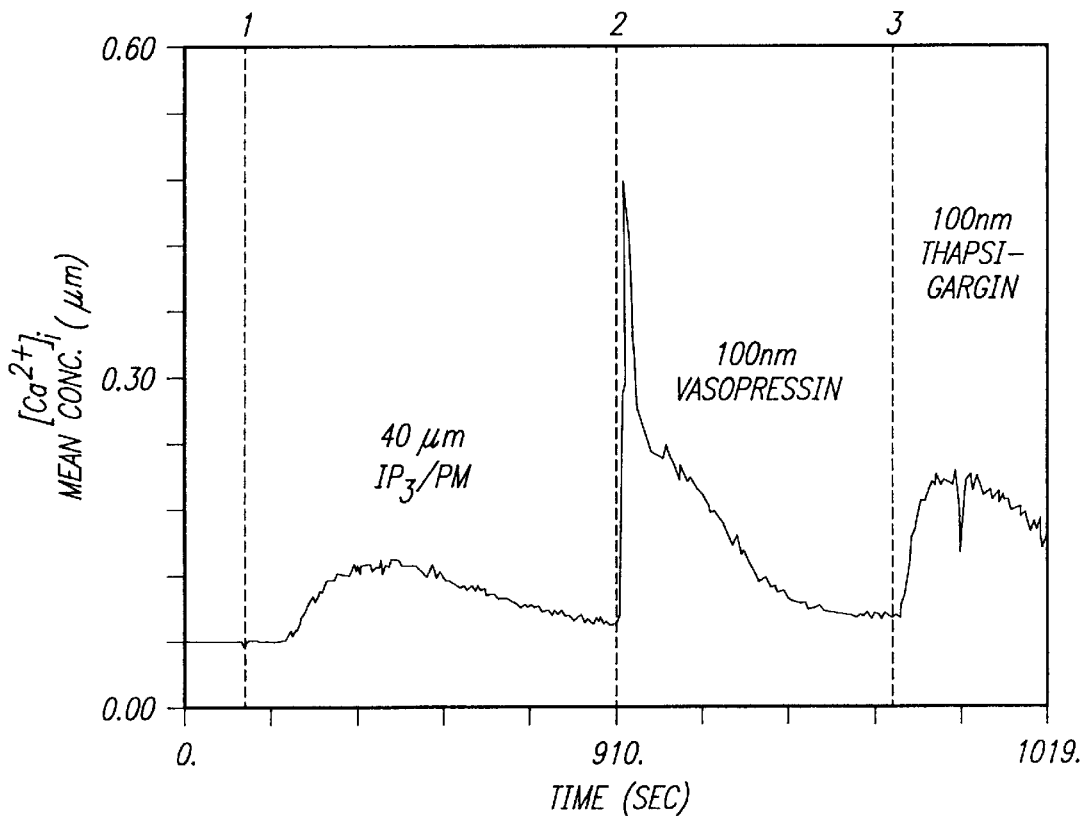
FIG. 6 depicts test results showing permeation of inositol triphosphate propionyloxymethyl ester ($IP_3/PM$) into REF-52 fibroblast cells.

The best-established biological effect of IP$_3$ is to release Ca$^{2+}$ from internal stores (26), so IP$_3$/PM (5a, R=Et, R'=H) was tested by imaging cytosolic free Ca$^{2+}$ levels in single REF-52 fibroblasts using standard methodology (58). Cells were loaded with the Ca$^{2+}$-indicator fura-2 and viewed by fluorescence excitation ratioing. IP$_3$/PM (40 μM) was applied extracellularly while monitoring cytosolic Ca$^{2+}$ concentrations. As shown in FIG. 6, the Ca$^{2+}$ concentration increased rapidly after addition of IP$_3$/PM (vertical dotted line labeled 1). Subsequent addition of vasopressin (vertical dotted line labeled 2), a well-known Ca$^{2+}$-releasing hormone (59) had much less effect than normal. This occlusion demonstrates that IP$_3$/PM had already partially exhausted the same pathways to elevate Ca$^{2+}$ as utilized by a physiological agonist, vasopressin.

Figure 7:
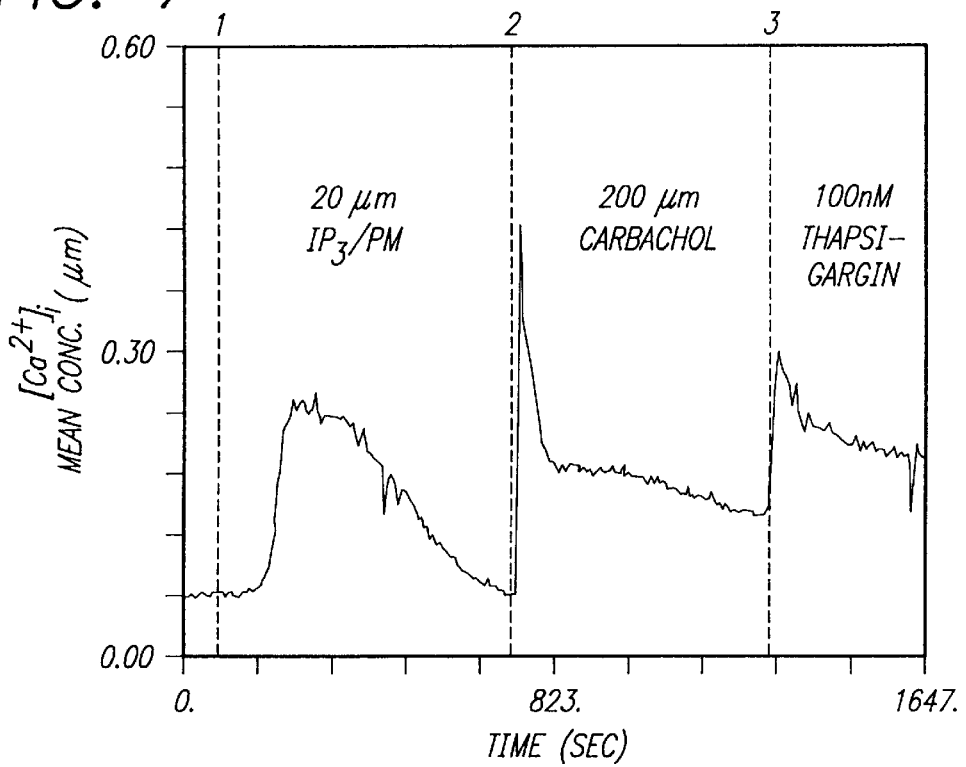
FIGS. 7 depicts test results showing permeation of IP3/PM into astrocytoma cells at a dose of 20 μm in a medium containing extracellular $Ca^{2+}$.

Biological tests on 1321N1 astrocytoma cells were performed similarly to the tests on REF-52 cells (71). The results of the tests are shown in FIG. 7. The concentration of Cytosolic free Ca$^{2+}$ (ordinate, in units of μM) in fura-2-loaded 1321N1 astrocytoma cells is shown as a function of time (abscissa, in units of seconds). At the dotted vertical line labeled 1, 20 μM inositol-1,4,5-triphosphate propionyloxymethyl ester (5a, R=Et, R'=H) was added. A sizable elevation of cytosolic Ca$^{2+}$ was observed after about 100 second delay. Subsequently the cells could respond to carbachol (200 μM, delivered at the dotted vertical line labeled 2), a drug that stimulates the endogenous generation of inositol-1,4,5-triphosphate. However, the response to carbachol is depressed by the prior treatment with the inositol-1,4,5-triphosphate propionyloxymethyl ester. Likewise the Ca$^{2+}$ response to thapsigargin (100 nM, delivered at the dotted vertical line labeled 3), another drug that releases stored Ca$^{2+}$, is depressed.

A test similar to the one shown in FIG. 7 was conducted except that the medium lacked extracellular Ca$^{2+}$ and a dose of 60 μM inositol-1,4,5-triphosphate propionyloxymethyl ester was added at the dotted vertical line labeled 1. The results of the test are shown in FIG. 8. A sizable elevation of cytosolic Ca$^{2+}$ was observed after about a 50 second delay. Because no extracellular Ca$^{2+}$ was present, this response must have represented release from intracellular Ca$^{2+}$ stores. Subsequently the cells' response to carbachol (200 μM, delivered at the dotted vertical labeled 2) was greatly depressed by the prior treatment with the inositol-1,4,5-triphosphate propionyloxymethyl ester. The much greater degree of inhibition of the carbachol response compared to the previous example (FIG. 7) is due to the higher dose of the inositol-1,4,5-triphosphate propionyloxymethyl ester and the absence of extracellular Ca$^{2+}$, which reduces refilling of Ca$^{2+}$ stores.

Figure 9:
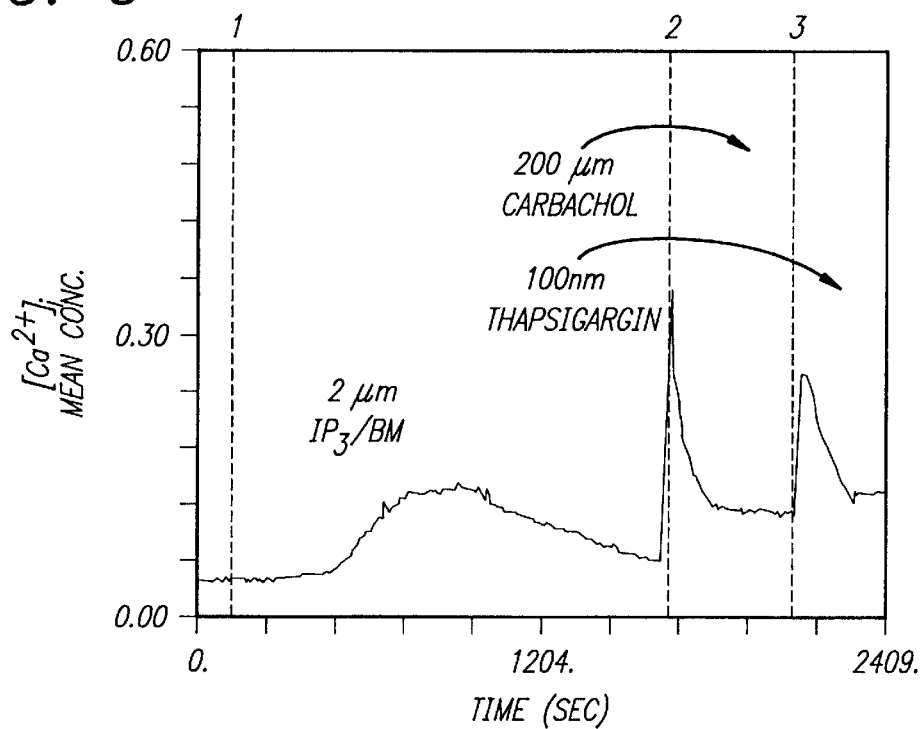
FIG. 9 depicts test results showing permeation of inositol triphosphate butyryloxymethyl ester ($IP_3/BM$) into astrocytoma cells at a dose of 2 μm in a medium containing extracellular $Ca^{2+}$.

In a further example, the same test as set forth above was conducted with astrocytoma cells, except that 2 μM inositol-1,4,5-triphosphate butyryloxymethyl ester (5a, R=Pr, R'=H) was used instead of the propionyloxymethyl ester. The test results are shown in FIG. 9. The butyryloxymethyl ester is somewhat more potent but its effects are slower to appear and decay.

The above biological results show that neutral, hydrophobic, membrane-permeant derivatives of inositol phosphates can be synthesized and show the expected biological activity when applied extracellularly to intact REF-52 fibroblasts and astrocytoma cells. IP$_3$/PM released Ca$^{2+}$ from internal stores, as would be expected for an agent that mimicked IP$_3$.

The above membrane-permeant derivatives of inositol polyphosphates utilize acyloxy groups esterifying all the phosphates to mask their negative charges. After crossing the plasma membrane, the compounds gradually hydrolyze inside the cell. As a result, both inositol phosphate release and the subsequent internal calcium release develops with a sigmoidal time course. The accumulation of active species can be limited because inositol phosphate may be destroyed by metabolic enzymes at rates comparable to its release from the protected form. Furthermore, if the hydroxyl groups are left free and unprotected, migration of phosphate esters to vicinal hydroxyls, reduction of the efficiency of delivery, and loss of pharmacological specificity may occur. Caging of the membrane-permeant inositol phosphate esters provides at least two improvements. First, all the hydroxyl groups are blocked by protecting groups, eliminating phosphate migration and increasing the efficiency and isomeric specificity of inositol phosphate delivery. Second, after entering the cell and undergoing hydrolysis, the caged inositol phosphate remains inactive because a key hydroxyl group, the 6-hydroxyl, is caged by a photolabile protecting group. This group should also block metabolic degradation, thereby helping caged $IP_3$ (structure 5 in FIG. 10) accumulate inside cells. Upon uncaging with UV light, the caged compound releases active species that cause a sudden $[Ca^{2+}]_i$ increase mimicking the one generated by physiological agonist stimulation.

The above-described caged inositol polyphosphate esters in accordance with the present invention have the following formulas:

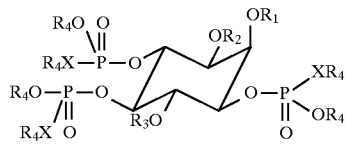

Wherein $R_1$ is H, —CHO, $COOCH_3$ or —$COCH_3$; $R_2$ is H or —P(O)(OR$_4$)(XR$_4$); or $R_1$ and $R_2$ together are —$CH_2$—, —CHMe—, —CMe$_2$—, —CH(OMe)—, —CMe(OMe)— or —C(OMe)$_2$—; $R_3$ is a photolabile protecting group;

$R_4$

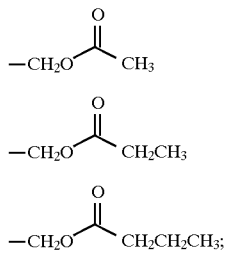

and

X is O or S.

When $R_1$ and $R_2$ taken together are —$CH_2$—, the compound has the formula

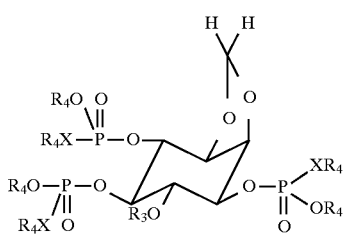

Likewise, when $R_1$ and $R_2$ taken together are —CH(OMe)—, the compound has the formula:

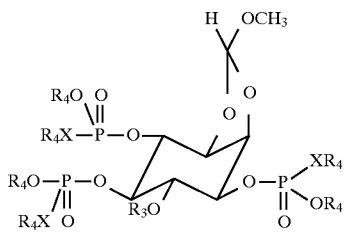

Preferred compounds are those where X is O.

The photolabile protecting group ($R_3$) may be any of the known compounds which are used to provide photolabile protection of reactive sites (see Reference 73). Exemplary photolabile protecting groups ($R_3$) include $R_5$, —$CH_2OR_5$ or —$COOR_5$ where R5 is

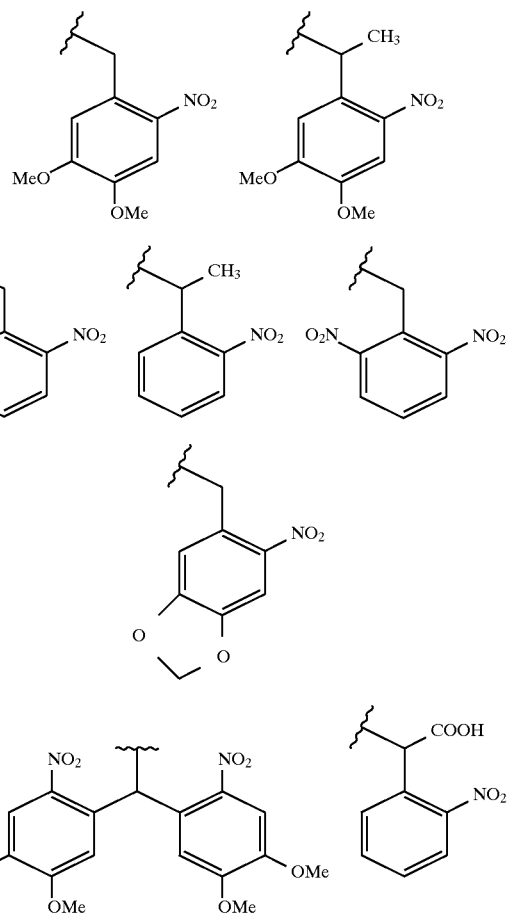

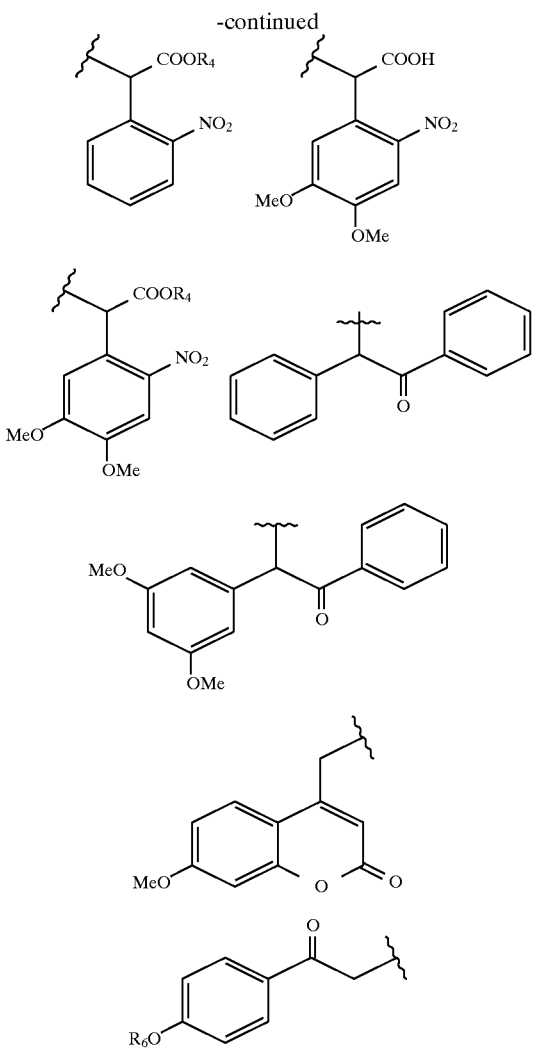

$R_6$=H, Me, $CH_3CO$ and $R_4$ is as defined previously.

Figure 10:
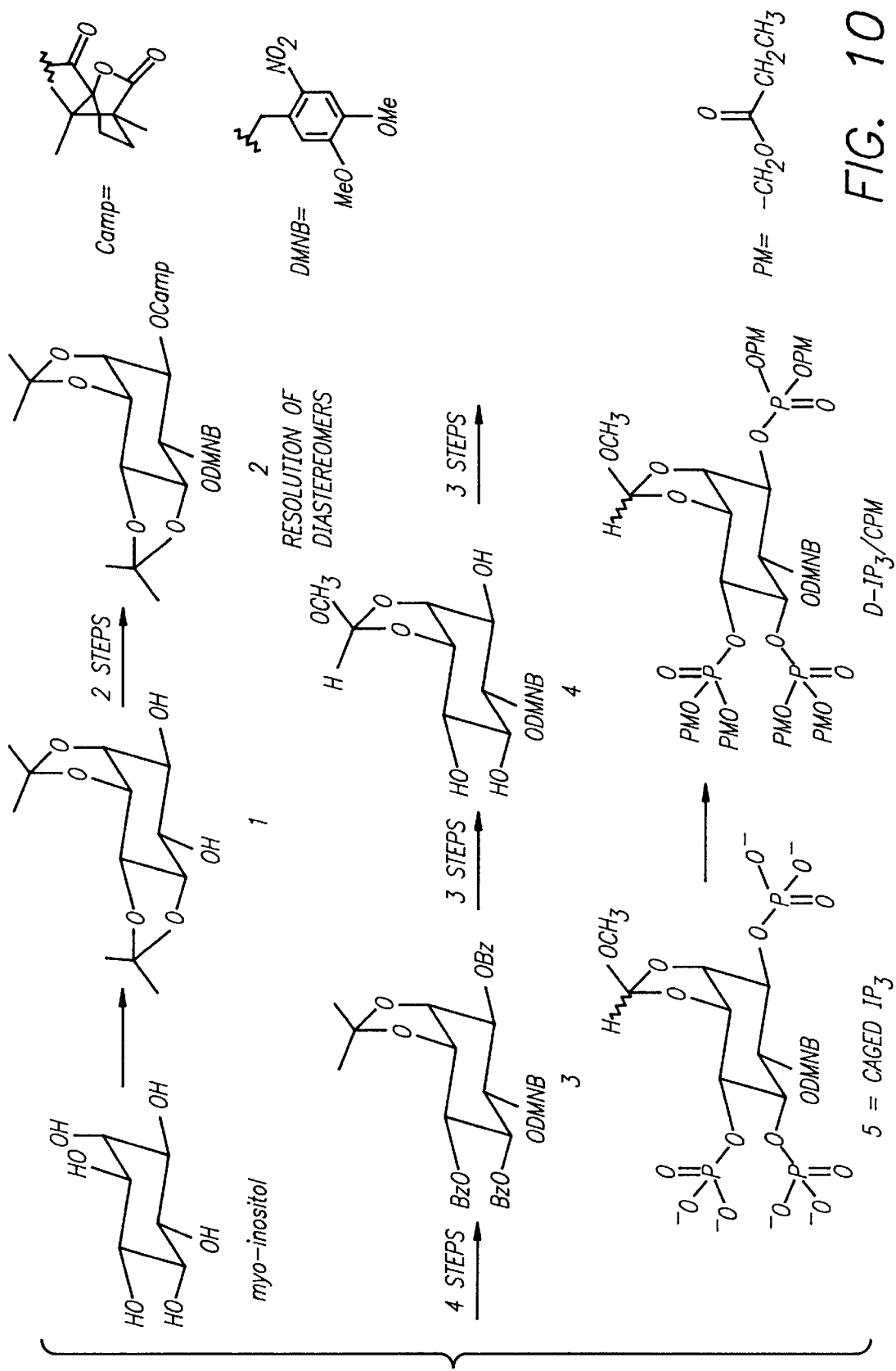
FIG. 10 is a schematic representation of the synthesis of exemplary caged esters of inositol phosphates.
Figure 11:
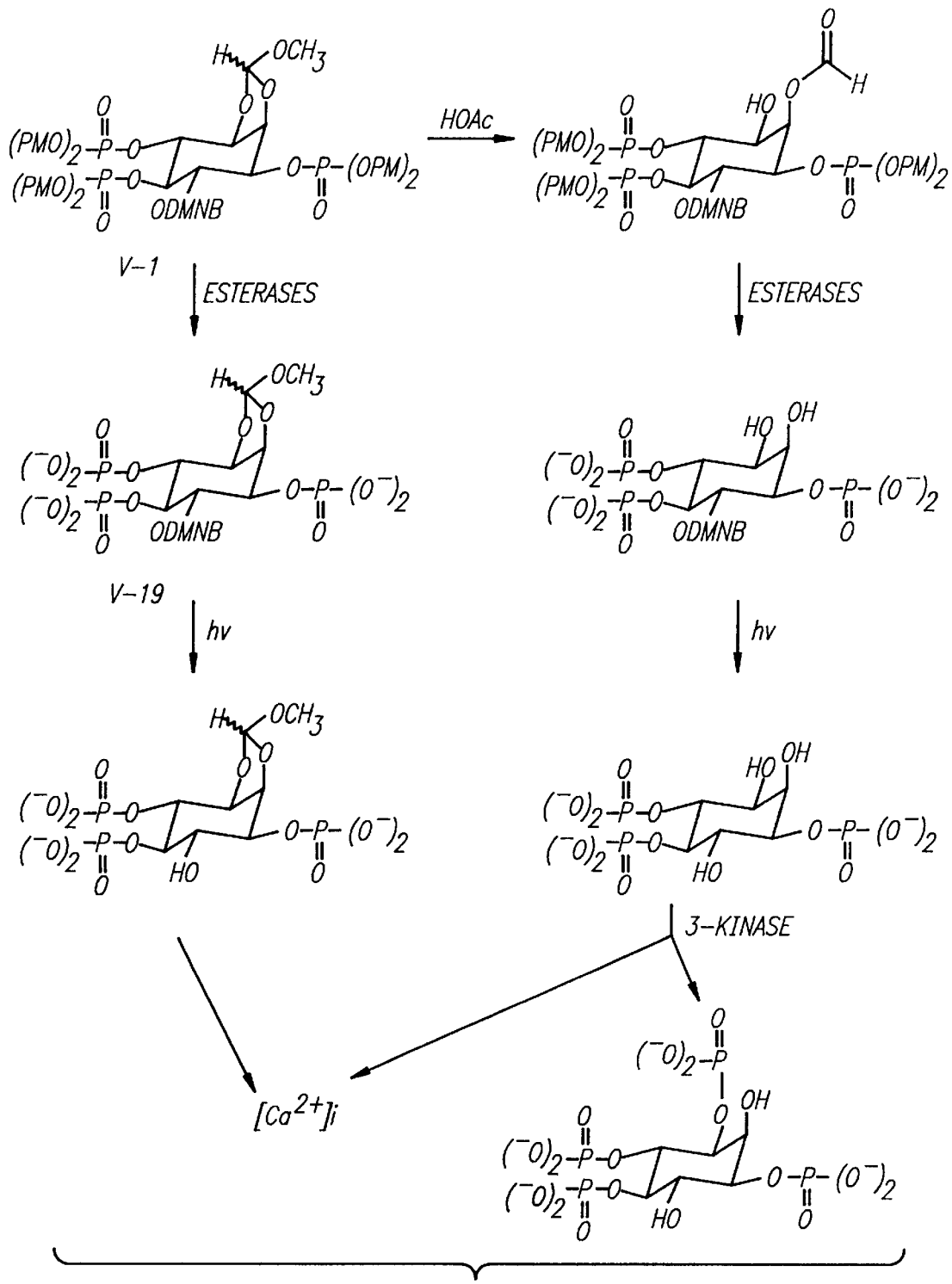
FIG. 11 shows exemplary preferred caged esters of inositol phosphates.

Examples of synthesis and use of the above identified caged compounds is as follows:

The general synthetic route to a preferred exemplary caged compound (D-IP$_3$/PM) is outlined in FIG. 10. A key step is to protect the 6-hydroxyl of inositol, which plays a critical role in binding to the IP$_3$ receptor and releasing calcium, with the photoliable group 4,5-dimethoxy-2-nitrobenzyl (DMNB). The 2- and 3-positions are covered by an orthoformate. Phosphorylation of 4 and esterification of the resulting trisphosphate 5 (caged IP$_3$) with bromomethyl propionate afforded IP$_3$/PM. The strategy is general enough to make other caged membrane-permeant IP$_3$ derivatives with different substituents on 2- and 3-position. In addition, this general procedure allows replacement of the phosphate by phosphothioate, which is metabolically more stable and has potential in drug development.

The 2-nitrobenzyl group and its derivatives 1-(2-nitrophenyl)ethyl, 4,5-dimethoxy-2-nitrobenzyl, and α-carboxy-4,5-dimethoxy-2-nitrobenzyl, have been widely used in caging biomolecules. These groups mask the charged (i.e. carboxylate or phosphate) or polar (i.e. amine or hydroxyl) functionalities of the molecules and increase their hydrophobicity, often increasing their membrane permeability. Before photolysis, these caged compounds are required to be biologically inactive because at least one of the key functionalities is blocked. However, the activity of the molecule can be triggered by a pulse of UV light (360 nm) because the nitrobenzyl group and its derivatives are photolabile. This strategy is very valuable for in vivo biological application. It allows control of the onset of bioactivity in living cells with millisecond temporal precision. The mechanism of this photo-transformation and the applications of caging compounds have been reviewed (72, 73). A few examples of caged molecules which have had successful applications in biology include caged cAMP (74,75), caged nitric oxide (76,77), caged fluorescein (78), caged calcium (79,80), caged glutamate (81–83), and caged IP$_3$ (84).

Commercially available caged inositol triphosphate (IP$_3$) has one of its vicinal phosphates (either the 4- or 5-phosphate, both of which play critical roles in binding to the IP$_3$R) esterified by a nitrophenylethyl group (85). The molecule still has over 3 negative charges at physiological pH and is membrane-impermeant, so that it can only be introduced into cells by techniques that disrupt their plasma membranes. The new caged and membrane-permeant IP$_3$ derivatives of the present invention have all phosphates covered by acyloxy asters and all the hydroxyls concealed by suitable protecting groups.

Among the commonly-used caging groups, 4,6-dimethoxy-2-nitrobenzyl (DMNB) group is preferred as the protecting group for the 6-hydroxyl. Compared to other photolabilo groups such as nitrobenzyl (NS) or nitrophenylethyl (NPE), the absorbance maximum of DMNB is at longer wavelengths (360 nm). Even though the quantum yield of DMNB for the photorelease was relatively low, its relatively high extinction coefficient at 360 nm (~5000 $M^{-1}cm^{-1}$) increases the overall uncaging efficiency (72,75). The methoxymethylene group is preferred to protect the 2- and 3-hydroxyls for two reasons: firstly, it is relatively small and should not interfere with the binding to the IP$_3$R; secondly, this group is a mixed ortlioformate ester, which makes it very labile to acid hydrolysis and removable with acetic acid (86). An advantage of leaving the methoxymethylene on the 2,3-hydroxyls is that phosphate migration is completely prevented and the absence of hydrogen-bond donors aids membrane permeation. In addition, the final active product cannot be metabolized by the IP$_3$-3-kinase. However, if one wished to deliver authentic IP$_3$ that can be converted to 1,3,4,5-IP$_4$ in vivo, the 3-hydroxyl should be unmasked by acetic acid before administering to cells. The formyl group usually remains on the axial hydroxyl group (87). The structures of a preferred caged, membrane-permeant IP$_3$ derivative (IP$_3$-CPM) with and without the methoxymethylene is shown in FIG. 1, together with their expected mode of action The detailed synthesis of IP$_3$-CPM is set forth in FIGS. 12 and 13. The synthesis started from racemic diol III-27. This compound was purified by recrystallization from the mixture of three regio-isomors of myo-inositol bisacetoridle. The commercial availability of this compound provides a route to prepare tho intermediate, triol V-8 (see FIGS. 12 and 13). In order to cover the 6-hydroxyl with DMNB group, a regioselective alkylation method is needed. A few procedures have been published for selective benzylation of the 6-hydroxyl in the presence of the 1 hydroxyl. These include Garegg's phase-transfer reaction (BnBr, Bu$_4$NHSO$_4$, CH$_2$Cl$_2$, 5% NaOH, reflux)(93) and Fraser-Reid's tin chemistry (Bu$_2$SnO, SnBr, toluene, reflux) (88,89). Similar selectivity is achievable with DMNB bromide due to its structural similarity to benzyl bromide. Since nitrobenzyl groups are not very stable under strongly basic conditions (90), Fraser-Reid's method is preferred because this reaction is carried out under neutral conditions and gives better selectivity.

Figure 12:
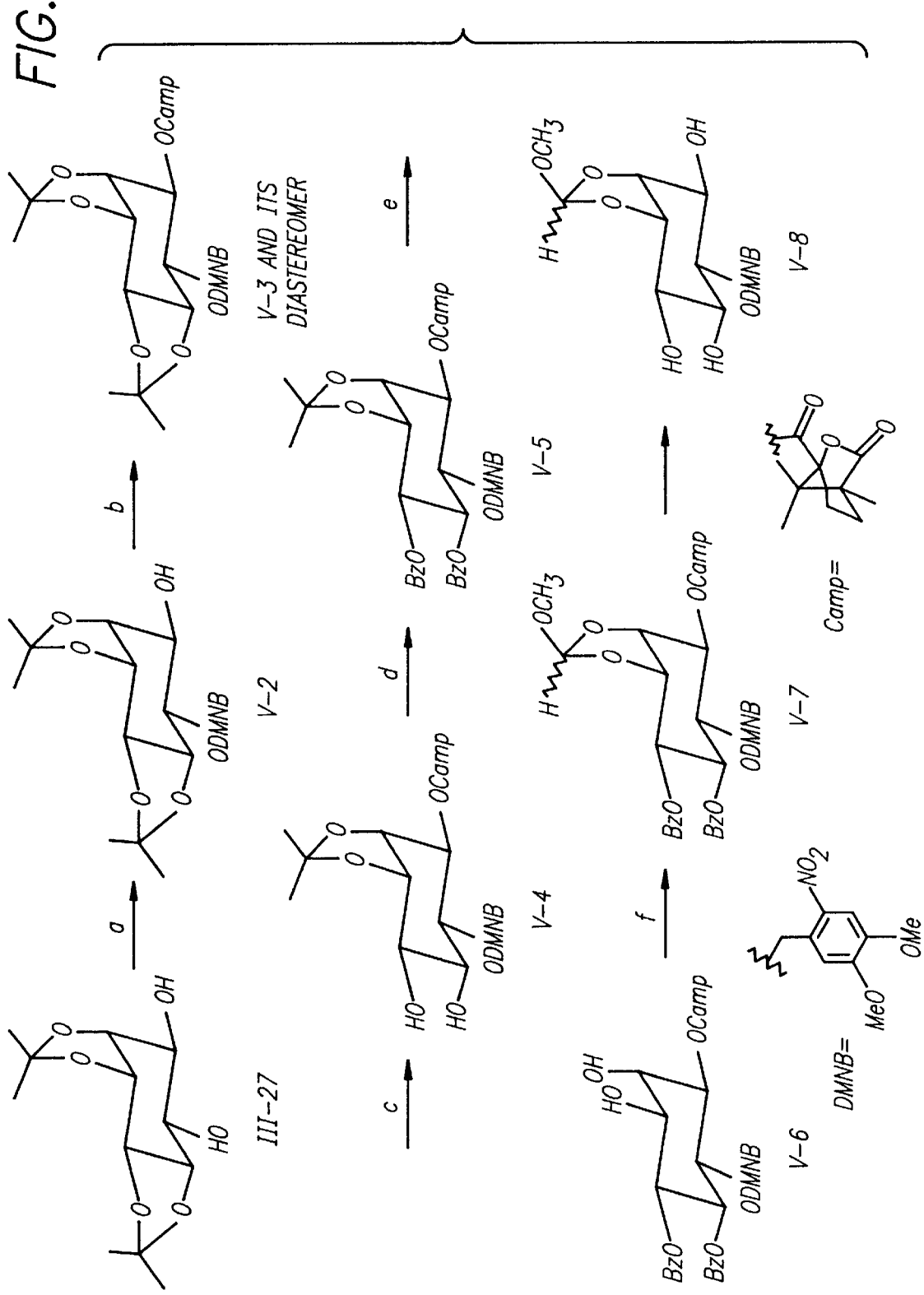
FIG. 12 shows details of the first portion of the synthesis of an exemplary caged inositol phosphate. The reference letters in the drawing refer to reagents used in each step as follows.
Figure 13:
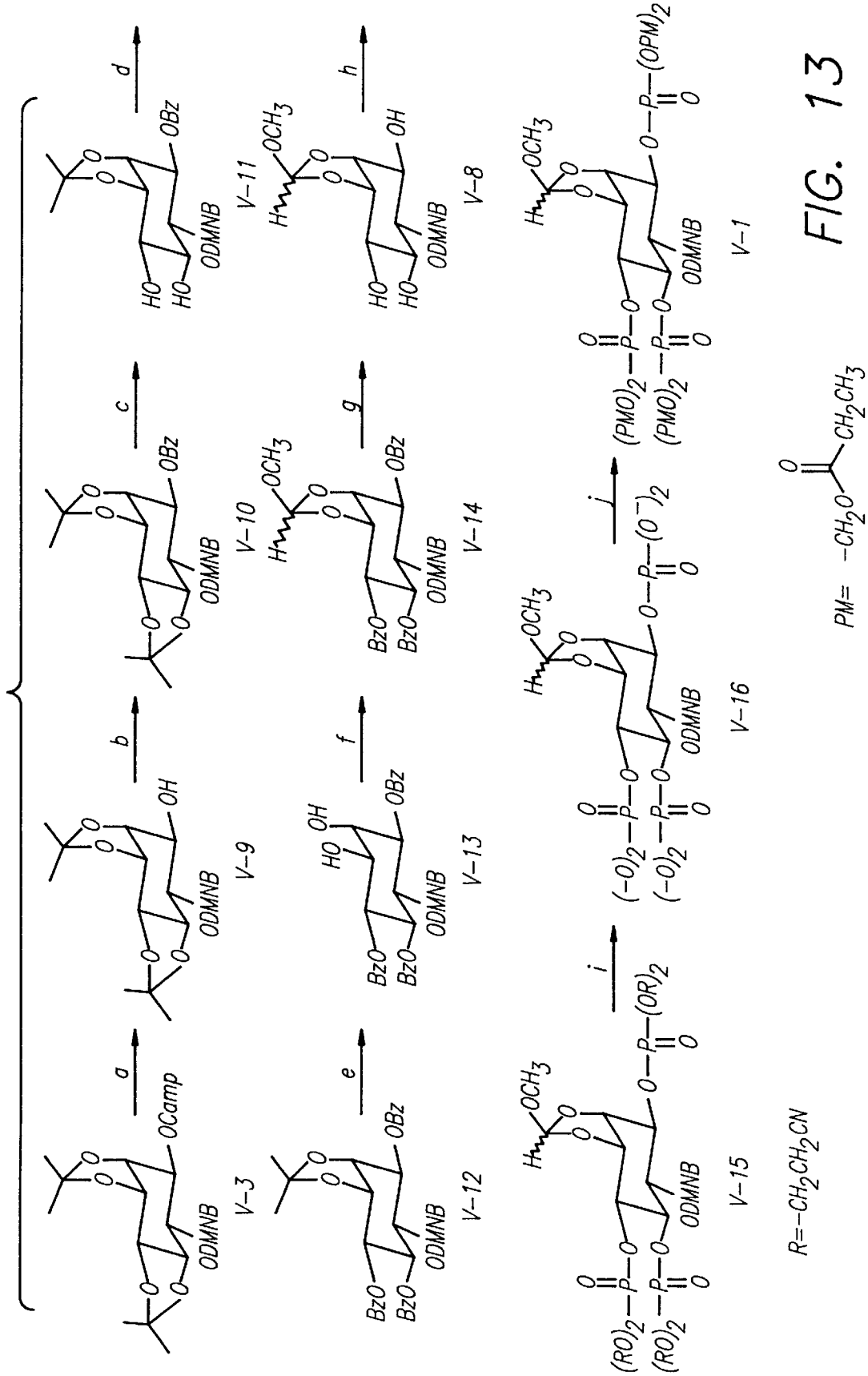
FIG. 13 shows details of the second portion of the synthesis of an exemplary caged inositol phosphate. The reference letters in the drawing refer to reagents used in each step as follows.

Thus, refluxing III-27 with dibutyl tinoxide gave a cyclized dibutylstannylene intermediate. The reaction was carried out in a Dean-Stark apparatus to remove water. Direct addition of DMNB bromide and cesium fluoride to the dibutylstannylene intermediate afforded monobenzylated product V-2 (FIG. 12). A very small amount of 1-benzylated isomer was also formed, but it could be removed by flash chromatography.

In order to resolve the racemic myo-inositol derivatives, V-2 was esterified with S-(−)-camphanic acid chloride to form a pair of diastereomers. S-(−)-camphanic acid chloride has been used before to resolve the racemic 4-O-benzyl-1, 2:5,6-di-O-cyclohexylidene-myo-inositol (91), which was structurally similar to V-2. After these two diastereomers are isolated as a mixture on a silica gel. 60 column, one of the isomers (V-3) can be selectively recrystallized out of the mixture. For comparison, another diastereomer, very close to V-3 on thin layer chromatography (TLC), was purified to homogeneity in small quantity by flash chromatography. The $^1$H-NMR spectra of these two compounds are very similar except that the chemical shift of one of the inositol ring-protons is different.

The trans-acetonide of V-3 was selectively removed in the presence of more stable cis-acetonide. Esterification of V4 and deprotection of cis-acetonide gave diol V-6. "Locking" the cis-diol of V-6 with methoxymethylene group turned out to be nontrival. Even with a large excess of trimethyl orthoformate and strong catalysts, such as p-TsOH, TMS triflate or boron trifluoride diethyl etherate, no product (V-7) was isolated. This problem appears to originate from the presence of the 1-O-camphanate, which might be too bulky and block the 2- and 3-hydroxyls. Accordingly, it is preferred that the camphanate of V-3 be replaced with benzoate and the diol V-13 prepared following the same synthetic route. This procedure is set forth in FIG. 13. Brief treatment of V-14 with acetic acid hydrolyzed methoxymethylene group and formed a formate on the axial 2-hydroxyl group, as shown by $^1$H-NMR. Methanolysis of V-14 gave the intermediate, triol V-8. Standard phosphitylation, oxidation and removal of β-cyanoethyl groups provided trisphosphate V-16 in 3 further steps.

Details of the synthesis are as follows:

Rac-2,3:4,5-di-O-isopropylidene-6-O-(4,5-dimethoxy-2-nitrobenzyl)-myo-inositol (V-2): Diol III-37 (2 g, 7.9 mmol) and dibutyltin oxide (2 g, 7.9 mmol) were refluxed in 50 mL anhydrous toluene in a Dean-Stark apparatus. The water formed during the reaction was removed from the organic phase. 3 h later, toluene was removed under vacuum. The residue was redissolved in 30 mL DMF. CsF (1.5 9, 10 mmol) and 4,5-dimethoxy-2-nitrobenzyl bromide(DMNB bromide, 3 g, 10.8 mmol) were then added and the mixture was-stirred vigorously at room temperature overnight. The mixture was diluted with 40 mL $CH_2Cl_2$ and filtered through a glass fiber filter. After removal of the solvent under vacuum, the residue was purified on a silica gel 60 column (hexane/acetono). 2.25 g of product was obtained as a pale yellow solid (63%). $^1$H-NMR ($CDCl_3$): δ 1.42–1.67(m, 12H, $CH_3$), 3.65(m, 1H), 3.9(dd, J=7.9, 1.8 Hz, 1H), 3.98(s, 3H, $OCH_3$), 4.05(s, 3H, $OCH_3$), 4.1 (m, 1H), 4.2(m, 1H), 4.4(t, J=7.2 Hz, 1H), 4.5(m, 1H), 5.1 (d, J=2.8 Hz, 2H, CH2), 7.38(s, 1H), 7.76(s, 1H).

D-2,3;4,5-di-O-isopropylidene-6-O-(4,5-dimothoxy-2-nitrobenzyl)-myo-nositol 1-(S)camphanate (V-3): Compound V-2 (3.07 g, 6.75 mmol) was dissolved in 70 mL $CH_2Cl_2$. Triethylamine (2.4 mL, 17 mmol) and a catalytic amount of 4-dimethylaminopyridine (DMAP, 50 mg) were included. S-(−)-camphanic acid chloride (1.7 g, 7.8 mmol) was added in one portion at 0° C. After stirring at room temperature for 3h, the solvent was removed and the residue was purified on a silica gel 60 column ($Et_2O/CH_2Cl_2$). 4.28 g of product (100%) which contained both diastereomers was obtained. This was further separated by recrystallization from acetone/hexane (200 mL, ~1:1). 1.35 g of crystalline material was obtained from the first crop. The second crop gave another 0.40 g crystal which was the same diastersomer as the first crop as judged from $^1$H-NMR. This was later confirmed to be D-isomer by $IP_2$ binding assay. $^1$H-NMR ($CDCl_3$) δ 0.9–2.05 (m, 12H), 2.45(m, 1H), 3.58(t, J=9 Hz, 1H), 3.84–4.02(m, 7H), 4.37(dd, J=8.2. 6 Hz. 1H), 4.63(t, J=4.6 Hz, 1H), 5.1–5.3 (m, 4H), 7.35(s, 1H), 7.7(s, 1H). Aliquots of mother liquor was purified again on flash chromatography (silica gel 60, $E(2O/CH_2Cl_2)$ to obtain a small sample of L-diastereomer for comparison. L-2,3:4,5-di-O-isopropylidene-6-O-(4,5-dimethoxy-2-nitrobenzyl)-myo-inositol 1-camphanate was a little bit more polar than its D-diastereomer on TLC. $^1$H-NMR ($CDCl_3$): δ 0.9–2.05 (m, 12H), 2.45(m, 1H), 3.58(t, J=9 Hz, 1H), 3.84–4.02(m, 7H), 4.37(dd, J=8.2, 6Hz, 1H),4.58(t, J=4.6 Hz, 1H), 5.1–5.3 (m, 4H), 7.29(s, 1H), 7.7(s, 1H).

D-2,3 :4,5-di-O-isopropylidene-6-O-(4,5-dimethoxy-2-nitrobenzyl)-myo-inositol (V-9): Compound V-3 (1.81 g, 2.85 mmol) was saponified overnight in 25 mL $CH_2Cl_2$ and 5 mL MeOH containing 1.5 g of $K_2CO_3$. The mixture was filtered through a glass fiber filter and concentrated. It was then purified on a silica gel 60 column and used directly for the next step.

D-2,3:4,5-di-O-isopropylidene-6-O-(4,5-dimethoxy-2-nitrobenzyl)-1-O-benzoyl-myo-inositol (V-1 0): The above compound and a small amount of DMAP (50 mg) was dissolved in 15 mL pyridine. The mixture was stirred at room temperature for 1h and the solvent was removed under vacuum. The residue was partitioned between $CH_2Cl_2$ and $NH_4Cl$ solution. The organic layer was dried over $Na_2SO_4$ and concentrated. It was purified on a silica gel 60 column and used directly for the next step.

D-2,3-O-isopropylidene-6-O-(4,5-dimethoxy-2-nitrobenzyl)-1-O-benzoyl-myo-inositol (V-11): The above compound V-10 was dissolved in 10 mL $CH_2Cl_2$ containing 2-mercaptoethanol(0.39 mL, 5.6 mmol). Boron trifluoride diethyl etherate (0.13 mL, 0.5 mmol) was then added. The reaction was monitored by TLC. In about half an hour the mixture was purified on a silica gel 60 column ($CH_2Cl_2$/MeOH). $^1$H-NMR ($CDCl_3$): δ 1.35(s, $CH_3$), 1.55(s, $CH_3$), 3.65(t, 1H), 3.85–4.2(m, 9H), 4.55(t, 1H), 5.1 (d, 1H), 5.35(d, 1H), 5.47(dd, 1H), 7.1–7.6(m, 5H), 7.95(m, 2H).

D-2,3-O-isopropylidene-6-O-(4,5-dimethoxy-2-nitrobenzyl)-1,4,5-tri-O-benzoyl-myo-inositol (V-12): Diol V-11 (0.65 g, 1.26 mmol) was dissolved in 4 mL pyridine containing a catalytic amount of DMAP (30 mg). Benzoyl chloride (0.44 mL, 3,78 mmol) was added in portion and the reaction was continued at room temperature for 2 h. After removal of the solvent under vacuum, the residue was partitioned between $CH_2Cl_2$ and $NH_4Cl$ solution. The organic layer was dried over $Na_2SO_4$ and concentrated. It was purified on a silica gel 60 column and 0.8 g of pale yellow syrup (94%) was obtained. This material was used directly for the next step.

D-6-O-(4,5-dimethoxy-2-nitrobenzyl)-1,4,5-tri-O-benzoyl-myo-inositol (V-13): Compound V-12 (0.8 g, 1.1 mmol) was dissolved in 10 mL $CH_2Cl_2$ containing 2-mercaptoethanol(0.31 mL, 4.4 mmol). Boron trifluoride diethyl etherate (0.05 mL, 0.19 mmol) was then added. The reaction was monitored by TLC. In 3h, the reaction was quenched by adding triethylamine (60 μL). The product was purified on a silica gel 60 column (toluene/ethyl acetate) and 0.6 g of light yellow solid (80%) was yielded. $^1$H-NMR (CDCl$_3$): δ 3.7(s, 3H, OCH$_3$), 3.85(s, 3H, OCH$_3$), 4.0(dd, J=9.5, 2.7 Hz, 1H, H$_3$), 4.35(t, J=2.6 Hz, 1H, H2), 4.58(t, J=10 Hz, 1H, H$_6$), 5.0–5.25(m, 2H), 5.3(dd, J=10.1, 2.6 Hz, 1H, H$_1$), 5.6–5.85(m, 2H, H$_4$/H$_5$), 7.1–8.15(m, 17H).

D-2,3-O-methoxymethylene-6-O-(4,5-dimethoxy-2-nitrobenzyl)-1,4,5-tri-O-benzoyl-myo-inositol (V-14): Diol V-13(0.6 g, 0.88 mmol) was mixed with 2 mL CH$_2$Cl$_2$ and 1 mL DMF. Boron trifluoride diethyl etherate (0.03 mL, 0.114 mmol) and excess trimethyl orthoformate (1 mL) were added. After 5 h at room temperature, the reaction was quenched by adding triethylamine (60 μL). The solvent was removed under vacuum and the residue was purified on a silica gel 60 column (hexane/ethyl acetate). 0.5 g of light yellow syrup (78%) was yielded and was used directly for the next step.

D-2,3-O-methoxymethylene-6-O-(4,5-dimethoxy-2-nitrobenzyl)-myo-inositol (V-8): V-14 (0.5 g, 0.69 mmol) was dissolved in 2 mL CH$_2$Cl$_2$ and 12 mL MeOH. K$_2$CO$_3$ (1.4 g, 10.3 mmol) was added, and the reaction was continued at room temperature for 24 h. The mixture was filtered through a glass fiber filter and concentrated. The residue was first passed through a short silica gel 60 column to remove salt. It was then purified on a silica gel 60 column (ethyl acetate/MeOH). A small amount of incompletely saponified products were eluted out before the desired product. One of them was dibenzoylated product, MS m/z 594.4(M-OCH$_3$)$^+$, expected 594.56 (C$_{31}$H$_{31}$O$_{13}$N$_1$-OCH$_3$)$^+$, and the other was monobenzoylated product, MS m/z 490.3 (M-OCH$_3$)$^+$, expected 490.45 (C$_{24}$H$_{27}$O$_{12}$N$_1$-OCH$_3$)$^+$. 150 mg of product was obtained as a pale yellow solid after dried in vacuum. $^1$H-NMR (CDCl$_3$ /d-MeOH, 10:1): δ 3.37(s, 3H, OCH$_3$),3.4–4.1 (m, 11H), 5.2(s, 3H), 5.37(t, 1H), 7.45(d, 1H), 7.52(s, 1H).MS m/z 386.1 (M-OCH$_3$)$^+$, expected 386.34(C$_{17}$H$_{23}$O$_{11}$N$_1$-OCH$_3$)$^+$.

D-2,3-O-methoxymethylone-6-O-(4,5-dimethoxy-2-nitrobenzyl)-myo-inositol 1,4,5-trisphosphate hexakis(β-cyanoethyl)ester (V-15): To a solution of 75 mg (0.18 mmol) of triol V-8 and 0.24 g (0.9 mmol) of N,N-diisopropyl-bis (β-cyanoethyl)phosphoramidite in 1 mL CH$_3$CN was added 49 mg (0.7 mmol) of tetrazole dissolved in 1 mL CH$_3$CN. After stirring at room temperature for 0.5 h, 0.4 mL tert-butyl hydroperoxide (3M solution in 2,2,4-trimethylpentane) in 1 mL CH$_2$Cl$_2$ was added in one portion at 0° C. After addition, the solution was warmed up to room temperature in 0.5 h and another 0.1 mL t-BuOOH solution was added. 10 min later, the solvent was removed under vacuum. The residue was loaded directly onto a silica gel 60 column and eluted with CH$_2$Cl$_2$/MeOH (15:1). Evaporation of solvent provided 0.14 g (79% for 2 steps) of product as a light yellow glass. MS m/z 944.39(M-OCH$_3$)$^+$, expected 944.69(C$_{35}$H$_{44}$O$_{20}$N$_7$P$_3$-OCH$_3$)$^+$.

D-2,3-O-methoxymethylene-6-O-(4,5-dimethoxy-2-nitrobenzyl)-myo-inositol 1,4,5-trisphosphate (V-16), ammonium salt: The above trisphosphate V-15 (0.14 g, 0.143 mmol) was suspended in 1 mL methanol and 6 mL concentrated NH$_4$OH. The solution was heated at 70° C. for 1.5 h and lyophilized. The resulting pale yellow solid was used directly for the next step.

D-2,3-O-methoxymethylene-6-O-(4,5-dimethoxy-2-nitrobenzyl)-myo-Inositol 1,4,5-trisphosphate hexakis (propionyloxymethyl)ester (V-1): Half of the above material was mixed vigorously with 0.5 mL CH$_3$CN and 0.1 mL DIEA. The mixture was then dried under vacuum. This procedure was repeated at least three times until a homogenous solution was obtained after adding CH$_3$CN/DIEA ( Sonication may be used to help solubilization). At this time, the counter-ion of the phosphate had presumably been exchanged from ammonium ion to diisopropylethylammonium ion. After a final round of drying, the pale yellow solid was suspended in 0.5 mL CH$_3$CN and 0.1 mL DIEA. 100 mg (0.55 mmol) of bromomethyl propionate was added to this solution. After stirring for 1 day, another 40 mg of bromomethyl propionate was added and the reaction was continued for another 24 h. The solvent and excess reagent were evaporated under vacuum. The remaining mixture was purified on silica gel column using ethyl acetate as eluant. 10 mg of product (12% for 2 steps) was obtained as a light yellow glass. $^{31}$P-NMR (CDCl$_3$): δ (-4.6, broad) MS: exact mass calcd for (C$_{41}$H$_{62}$O$_{32}$NP$_3$+Cs$^+$) 1305.1444, observed 1305.1481 (2.8 ppm).

D-2,3-O-methoxymethylene-6-O-(4,5-dimethoxy-2-nitrobenzyl)-myo-inositol 1,4,5-trisphosphate hexakis (acetoxymethyl)ester: This was synthesized in a similar manner as above except using bromomethyl acetate as esterification reagent. 8 mg product (10%) as a light yellow glass. $^{31}$P-NMR (CDCl$_3$): δ-4.55(s, 1P), -4.65(s, 2P). MS: exact mass calcd for (C$_{35}$H$_{50}$O$_{32}$NP$_3$+Cs$^+$) 1222.0583, observed 1222.0533 (4.1 ppm).

Exemplary Syntheses of Analogs of IP$_3$-CPM

To produce the compounds with R$_3$ being photolabile protecting groups other than 4,5-dimethoxy-2-nitrobenzyl as described above, the 4,5-dimethoxy-2-nitrobenzyl bromide presently used to convert III-37 to V-2 (see FIG. 12) is replaced by the chloride, bromide, iodide, or tosylate of the appropriate photolabile protecting group, i.e. (R$_3$)Cl, (R$_3$Br, (R$_3$)I, or (R$_3$)OTs.

To produce the compounds with R$_1$ and R$_2$ together being —CH$_2$—, —CHMe—, —CMe$_2$—, —CMe(OMe)—, or —C(OMe)$_2$—, the trimethyl orthoformate used in the preparation of V-14 (see FIG. 13) is replaced respectively by dimethoxymethane, acetaldehyde dimethyl acetal 2,2-dimethoxypropane, trimethyl orthoacetate, or tetramethyl orthocarbonate, as known in standard methods for preparing cyclic ketals and orthoesters.

Figure 16:
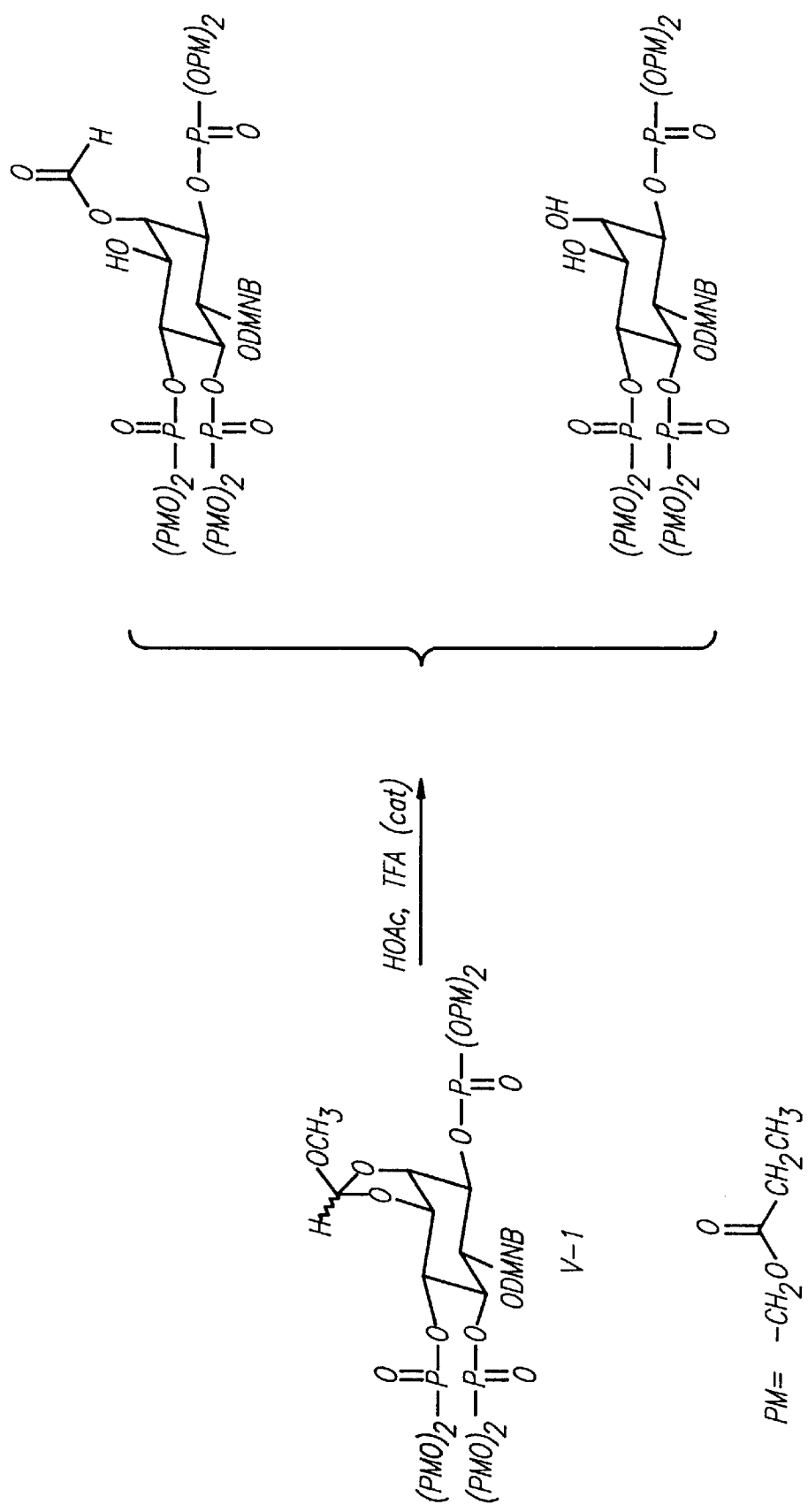
FIGS. 16–18 are diagrams of exemplary synthesis procedures for making compounds in accordance with the present invention.

To produce the structures R$_2$=H and R$_1$=H or —CHO, the synthetic scheme outlined in FIG. 16 can be followed. Brief incubation of V-1 with an acetic/trifluoroacetic acid mixture removes the methoxymethylene bridging the 2,3-hydroxyls and gives the above products, both of which have free 3-hydroxyls (R$_2$=H). Longer incubations will shift the product distribution towards de-esterification of the 2-hydroxyl (R$_1$=H). The same synthetic strategy is applicable to other acid labile groups, such as acetonide, orthoacetate, or orthocarbonate. For example, the structure with R$_1$=—COCH$_3$ would result from brief acid treatment of the orthoacetate, in which R$_1$ and R$_2$ together had been —CMe(OMe)—. The structure with R$_1$=—COOCH$_3$ would result from brief acid treatment of the orthocarbonate, in which R$_1$ and R$_2$ together had been —C(OMe)$_2$—.

Figure 17:
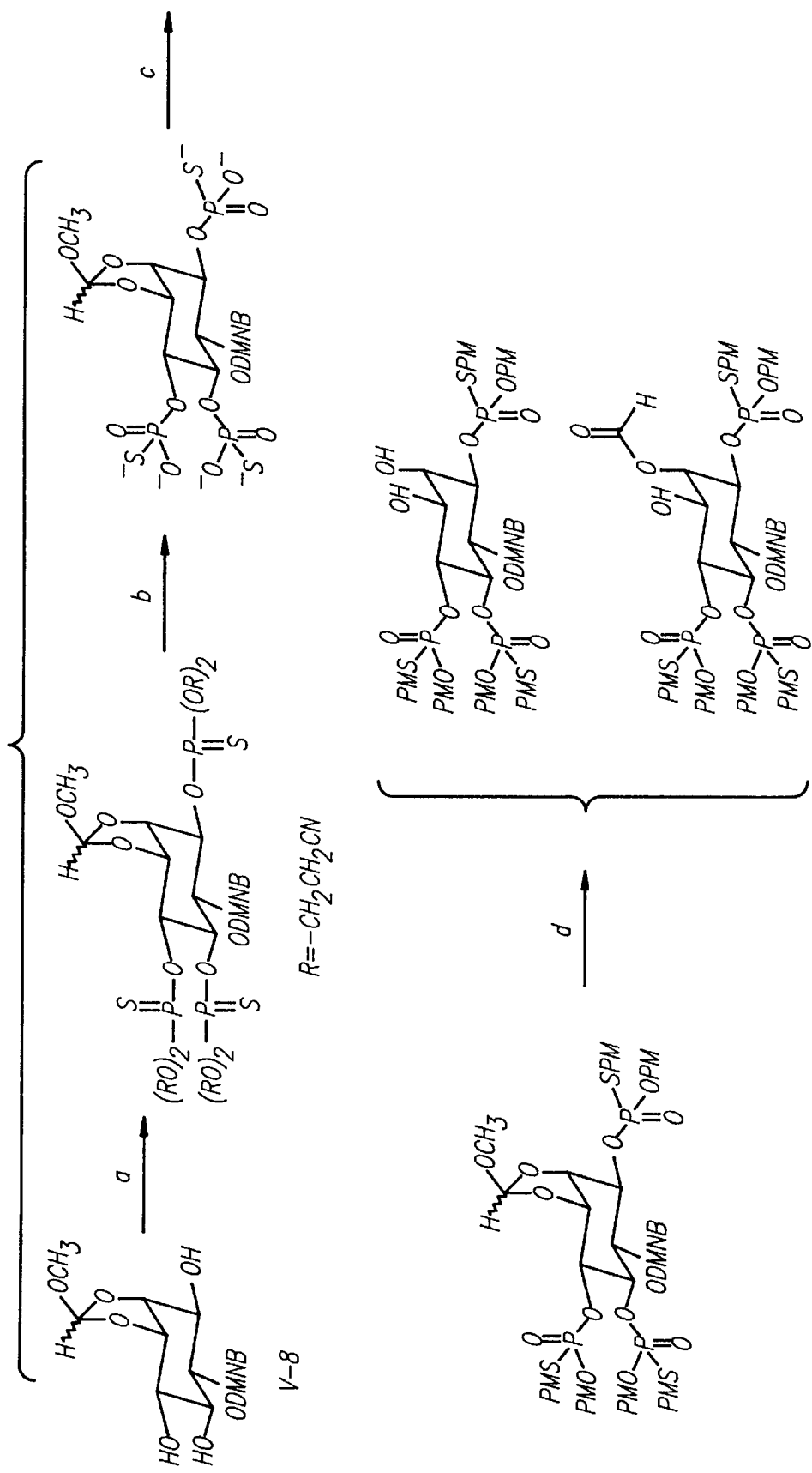

An exemplary synthesis procedure for making analogs where X=S, is set forth in FIG. 17. The tert-butyl hydroperoxide used in the synthesis of V-15 would be replaced by a sulfur donor such as benzoyl disulfide. For example, the caged membrane-permeant derivative of myo-inositol 1,4, 5-trisphosphorothioate (IPS$_3$-CPM) would be synthesized by a slight modification of the synthetic strategy used for making IP$_3$-CPM. Phosphitylation of triol V-8 gives a phosphite triester intermediate which provides the tris (phosphorothioate) upon treatment with benzoyl disulfide. Removal of β-cyanoethyl groups and esterification of the resulting tris(phosphorothioate) will give the target molecule with X=S. If a free 3-hydroxyl group is desired, the orthoformate or other acid labile moieties (acetonide, orthoacetate, or orthocarbonate) bridging the 2- and 3-positions can be similarly removed by acid treatment as described above.

An exemplary synthesis procedure for making analogs where $R_2 = -P(O)(OR_4)(XR_4)$, i.e.

Figure 18:
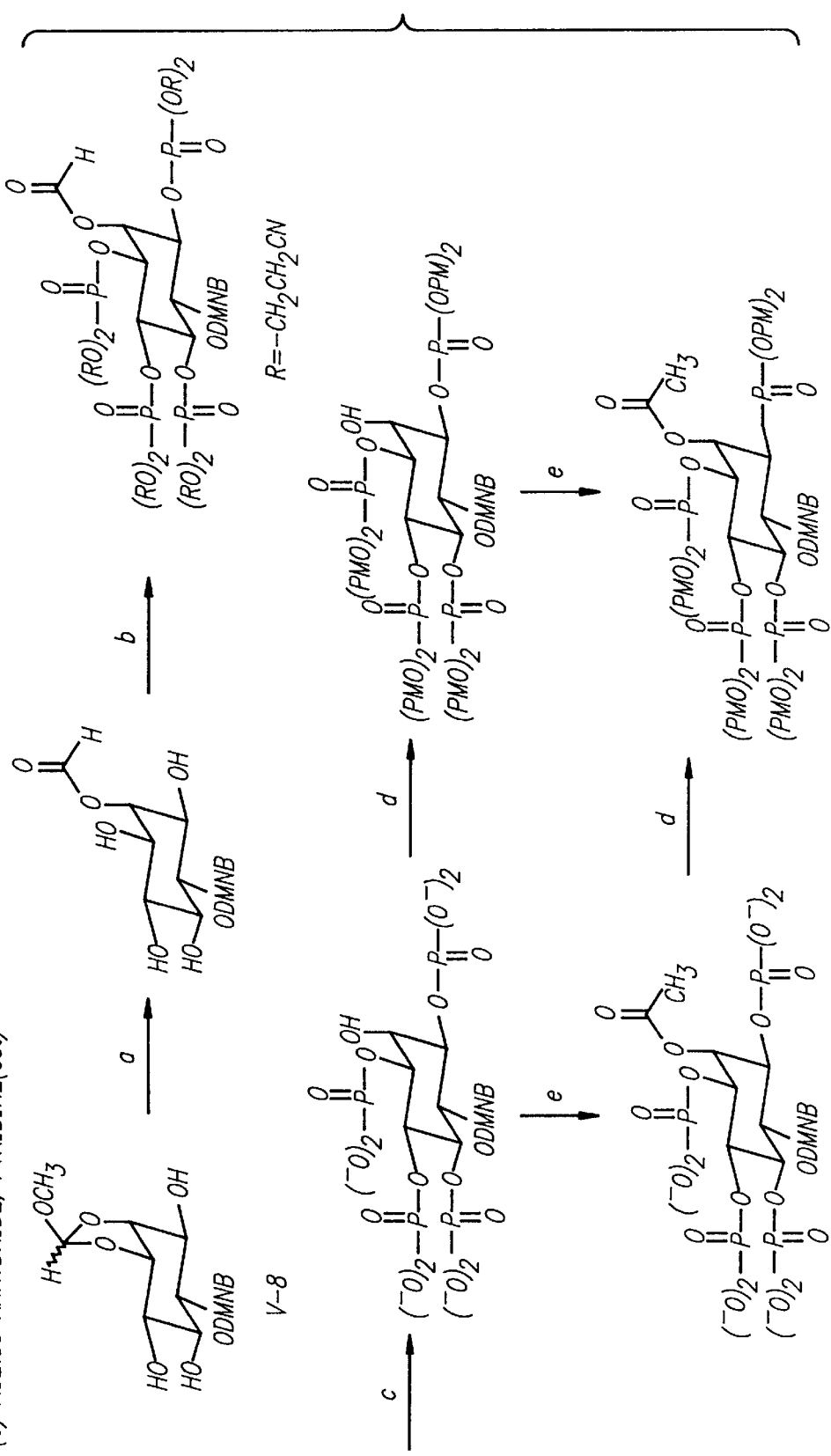

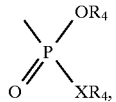

such as caged membrane-permeant myo-inositol 1,3,4,5-tetrakisphosphate ($IP_4$-CMP), is set forth in FIG. 18. The 3-hydroxyl of V-8 would be deprotected by acid (e.g. acetic acid with a catalytic amount of trifluoroacetic acid), leaving a formate ester on the 2-position. Standard phosphitylation, oxidation and removal of β-cyanoethyl groups analogous to the preparation of V-15 will install phosphates on the 1,3,4,5-positions. The 2-hydroxyl will be de-esterified in the process of cleaving the β-cyanoethyl groups with ammonia. Esterification of the tetrakisphosphates with bromomethyl acetate, propionate or butyrate yields the target molecules in which $R_1$=H. If $R_1$=—CHO, —$COCH_3$, or —$COOCH_3$ is desired, the 2-hydroxyl can be re-esterified at this stage using acetic formic anhydride, acetic anhydride, or methyl chloroformate respectively, since the 2-position carries the only free hydroxyl. It should be noted that step d in FIG. 17 and step 3 in FIG. 18 are optional and are needed only if one wishes $R_2$ to be H, i.e. for 3-hydroxyl to be free.

Bovine cerebellum microsomal fractions, which are a rich source of $IP_3$ binding protein, were prepared and used for [$^3$H]$IP_3$ binding assay. The preparation bound to [$^3$H]$IP_3$ with high affinity and the binding was competitively inhibited by cold D-$IP_3$ in a dose dependent manner. The $IC_{50}$ of D-$IP_3$ was about 8 nM. In agreement with the published data, L-$IP_3$ had negligible affinity to $IP_3$R. Thus, if V-16 was derived from D-isomer, its photolysed product, i.e. D-O-2,3-methoxymethylene-myo-inositol 1,4,5-trisphosphate, should have a high affinity to the $IP_3$R; otherwise its photolysed product would have minimum effect on the binding of [$^3$H]$IP_3$ to the receptor.

The caged $IP_3$ derivative V-16 showed negligible binding to cerebellar microsomes because its 6-hydroxyl was blocked. Upon photolysis at 366 nm, V-16 displayed a UV-dose-dependent increase of binding to the receptor. In about 2 hours, the binding leveled off because longer exposure to UV light did not change the binding activity significantly, indicating most of V-16 was photolyzed. At this point, the crude photolysis product from 100 pmol V-16 was equivalent in binding activity to 32 pmol of authentic $IP_3$. Assuming the chemical yield of the uncaged product is 100%, its affinity for the $IP_3$ receptor is only 3-fold weaker than that of real $IP_3$. If the chemical yield were lower than 100%, the affinity of the photolysis product would have to be even closer to that of $IP_3$. This example shows that the photolysis product of V-16 is D-2,3-methoxymethylene-myo-inositol 1,4,5-trisphosphate, which means that V-16 was derived from precursors of D-configuration. The absolute stereochemistry of V-3 and its diastereomer was thus assigned.

In Vivo Tests of Caged Membrane-Permeant $IP_3$

Figure 14A:
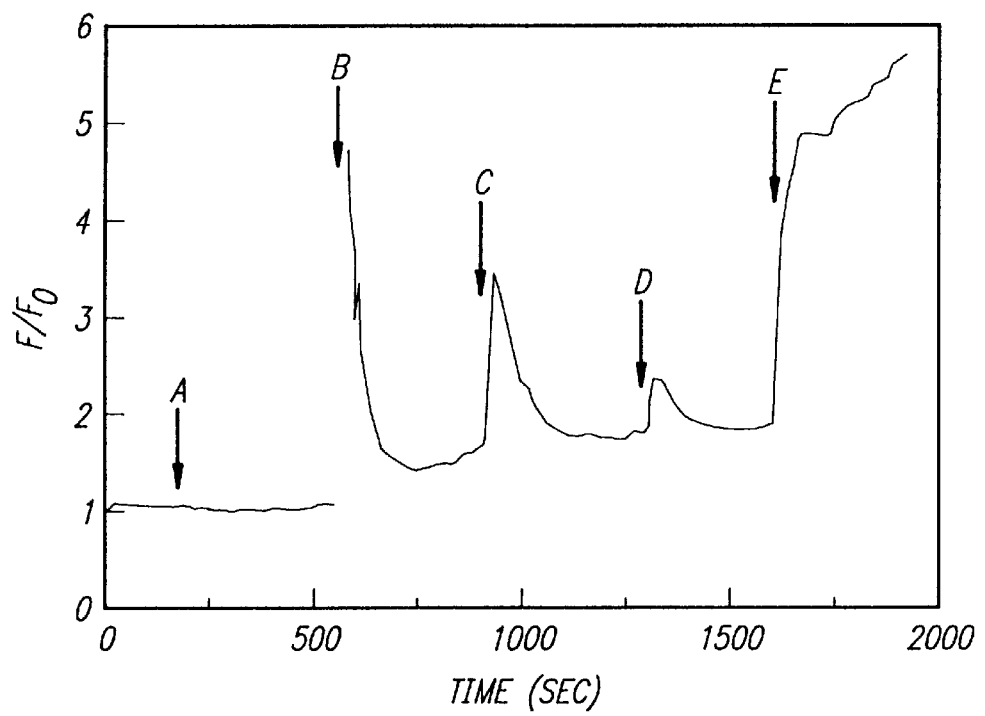
FIG. 14 shows the results of tests demonstrating IP$_3$-CPM (V-1) induced [Ca$^{2+}$]$_i$ increase upon uncaging. (a) Extracellular application of IP$_3$-CPM (A, 20 μM) had no effect on [Ca$^{2+}$]$_i$ even after incubation for about 5 minutes. Exposure of the cells to UV light (B, 360 nm, 10 s) caused an almost saturating [Ca$^{2+}$]$_i$ increase. The [Ca$^{2+}$]$_i$ level remained elevated above the resting level due to the Ca$^{2+}$ influx. Carbachol (C, 200 μM) and thapsigargin (D, 100 nM) gave normal response. Ionomycin (E, 5 μM) was added at the end of the experiment and gave a huge [Ca$^{2+}$]$_i$ increase. (b) Same experiment as (a) except done in Ca$^{2+}$ free medium (DPBS, O Ca$^{2+}$, 0.5 mM EGTA). UV exposure of the cells treated with IP$_3$-CPM still gave the same response, showing that the [Ca$^{2+}$]$_i$ increase resulted from the release of Ca$^{2+}$ from internal stores. The [Ca$^{2+}$]$_i$ level soon went back to the resting level because there was no extracellular Ca$^{2+}$ with which to maintain a [Ca$^{2+}$]$_i$ elevation. Ionomycin was added at the end of the experiment and gave an additional small [Ca$^{2+}$]$_i$ increase, probably from IP$_3$ insensitive stores. The cells were loaded with fluo-3/AM. During the experiment the cells were bathed in HBS buffered with 20 mM Hepes at pH 7.4 and supplemented with 2 g/L glucose.

In 1321N1 astrocytoma cells, extracellular addition of 20 μM $IP_3$-CPM had no effect on [$Ca^{2+}$]$_i$ even after incubation for over 5 minutes (FIG. 14(a)). The [$Ca^{2+}$]$_i$ was monitored using the calcium indicator fluo-3 rather than fura-2 to keep the excitation wavelength of the indicator (490 nm) far from the uncaging wavelength (360 nm) of DMNB group. Subsequent illumination of the cells with UV (360 nm) through the microscope objective for a short period of time (10 seconds) caused an almost saturating [$Ca^{2+}$]$_i$ increase. Compared to the photolyzing set-up (direct illumination by a hand mercury lamp) used for the $IP_3$-binding assay, the optical throughput from the source lamp to the specimen is much higher in a microscope, so 10 seconds (as opposed to 2 hours in $IP_3$ binding assay) of photolysis was sufficient to produce enough $IP_3$ to elicit [$Ca^{2+}$]$_i$ increase. The same amount of UV alone had no effect at all on [$Ca^{2+}$]$_i$ in cells not treated with $IP_3$-CPM. After recovering from uncaging of $IP_3$-CPM, the cells responded to subsequent carbachol and thapsigargin stimulation normally. Ionomycin further raised [$Ca^{2+}$]$_i$ to a saturating level.

Figure 14B:
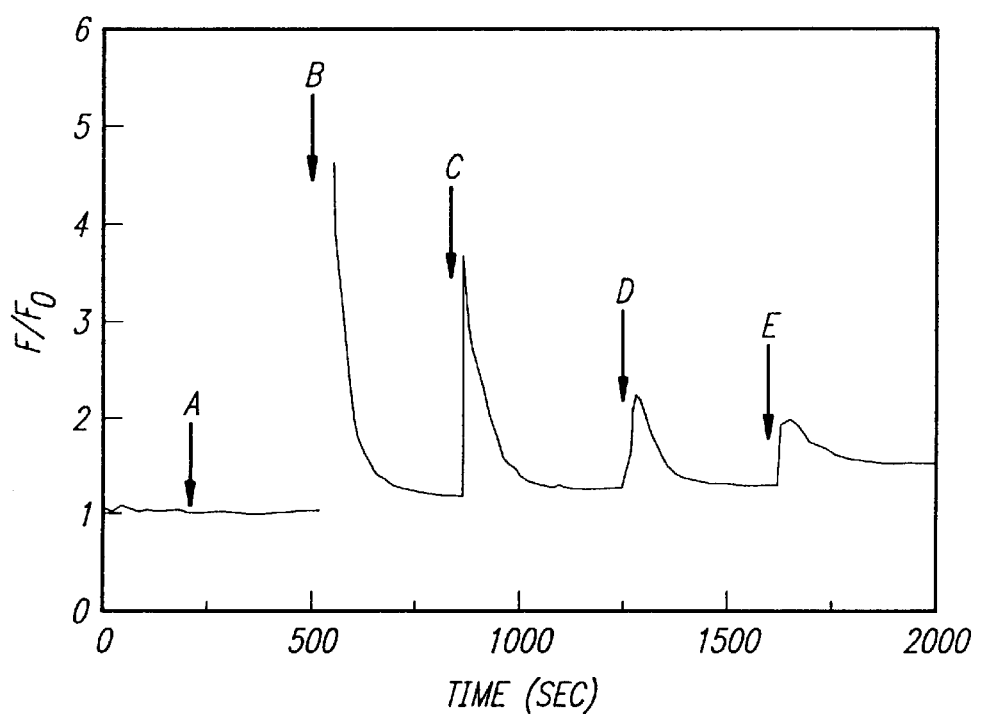

A similar response to $IP_3$-CPM was also observed when the experiment was done in calcium free medium (FIG. 14(b)). This confirmed that the [$Ca^{2+}$]$_i$ increase due to uncaging of $IP_3$-CPM resulted from internal $Ca^{2+}$ release, which was consistent with the normal mechanism of $IP_3$ action. Carbachol and thapsigargin were still able to cause further $Ca^{2+}$ release, suggesting that the internal stores were only partially emptied by the first dose of uncaged $IP_3$ analog, or that they had substantially refilled with $Ca^{2+}$ after that agonist had been metabolized. Ionomycin was added at the end of the experiment, but it only caused a small and transient [$Ca^{2+}$]$_i$ increase, possibly from some $IP_3$-insensitive stores.

Figure 15:
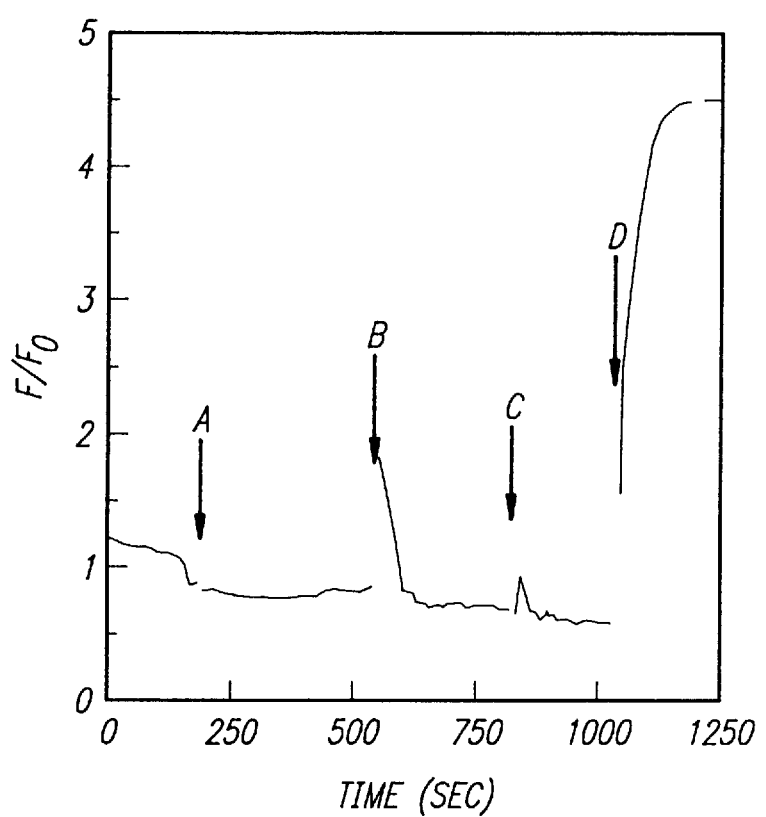
FIG. 15 shows the results of tests demonstrating IP$_3$-CPM (V-1) induced [Ca$^{2+}$]$_i$ increase upon uncaging in P388D$_1$ macrophage-like cells. Extracellular application IP$_3$-CPM (A, 20 μM) had no effect on [Ca$^{2+}$]$_i$ even after incubation for about 5 minutes. Exposure of the cells to UV light (B, 360 nm, 10 s) caused a big [Ca$^{2+}$]$_i$ increase. The [Ca$^{2+}$]$_i$ level went back to the basal level in a short time, indicating there was little Ca$^{2+}$ influx. PAF (C, 100 nM) stimulation gave attenuated response, possibly because the internal stores were not refilled yet. Ionomycin (D, 5 μM) was added at the end of the experiment and gave a huge [Ca$^{2+}$]$_i$ increase. The cells were loaded with fluo-3/AM. During the experiment the cells were bathed in HBS buffered with 20 mM Hepes at pH 7.4 and supplemented with 2 g/L glucose.

Another example was carried out in P388$D_1$ macrophage-like cells. The results were the same as the astrocytoma cells and are shown in FIG. 15.

Extracellular addition of 20 μM $IP_3$-CPM had no effect on [$Ca^{2+}$]$_i$ even after incubation for over 5 minutes. Photolysis for 10 seconds (360 nm) released a fair amount of $Ca^{2+}$ from internal stores. Compared to the experiments done in astrocytes, $Ca^{2+}$ influx in P388$D_1$ cells after uncaging was less obvious, and subsequent stimulation with PAF gave smaller [$Ca^{2+}$]$_i$ increase, possibly the internal stores were not refilled yet. Studies by Asmis et al. (92) have shown that, in P388$D_1$ macrophage-like cells, PAF stimulated $PGE_2$ production is mediated through two separate signals: $IP_3$ induced [$Ca^{2+}$]$_i$ increase and another unidentified signal. $IP_3$-CPM might serve as a new tool for detailed study of $PGE_2$ formation and AA release in relation to $IP_3$ and [$Ca^{2+}$]$_i$ in these cells. One of the major advantages of using permeant $IP_3$ derivatives is that experiments can be easily carried out in a population of cells, which is required for the measurement of AA release and $PGE_2$ formation.

The above examples show that $IP_3$-CPM crossed the cell membrane and its PM esters underwent intracellular hydrolysis. The resulting caged $IP_3$ analog (V-16) was inactive in releasing $Ca^{2+}$, which was consistent with the in vitro [$^3$H]$IP_3$ binding experiment. Upon photolysis, the caged $IP_3$ analog V-16 rapidly formed active D-2,3-methoxymethylene-myo-inositol 1,4,5-trisphosphate, which has an affinity to $IP_3$R at least one third that of $IP_3$, and induced internal $Ca^{2+}$ release. Furthermore, V-16, once it was released intracellularly, was well retained in cells and was also metabolically fairly stable.

In human embryonic kidney cells (HEK cells), the extracellular $IP_3$-CPM was washed away after the cells had been loaded with 50 μM of $IP_3$-CPM for 20 minutes. Photolysis of the cells in the field for 1 ms with a capacitor-discharge flash lamp resulted in a transient increase in [$Ca^{2+}$]$_i$. The ability of the cell's $[Ca^{2+}]_i$ to respond to each flash persisted for up to a dozen repetitions. Cells in the same dish which had not been exposed to UV light were kept in the dark for over 6 hours. Photolysis of these cells still gave $[Ca^{2+}]_i$ increases similar to those obtained immediately after being loaded with $IP_3$-CPM. This shows that caged $IP_3$ (V-16) was resistant to phosphatase degradation and could be trapped inside cells for a long period of time without losing much of its activity. The photolysis product of V-16 can not be phosphorylated into 1,3,4,5-$IP_4$. However, pretreatment of $IP_3$-CPM with acetic acid will unmask the 3-hydroxyl and enable the intracellular phosphorylation of delivered $IP_3$.

Another caged, membrane permeant $IP_3$ derivative, 1,4, 5-triphosphate hexakis (acetoxymethyl) ester ($IP_3$-CAM), was also synthesized from V-16 using AM bromide as esterification reagent. Biological tests of this compound in astrocytes gave similar response as $IP_3$-CPM, yet higher concentration of $IP_3$-CAM (30 $\mu$M) and longer incubation time (more than 15 minutes) were required, possibly because of the decreased membrane permeability of the prodrug.

As is apparent from the above examples, a number of caged and membrane-permeant $IP_3$ derivatives can be prepared using the above described general and specific procedures. These cage derivatives display a faster onset of activity which can be triggered by a flash of UV light and can be controlled with millisecond temporal resolution. In 1321N1 astrocytoma cells, extracellular concentrations of only $10^{-6}$ to $10^{-5}$M of $IP_3$-CPM were able to elicit maximal $Ca^{2+}$ release upon uncaging. In addition, $IP_3$-CPM has all the hydroxyls of $IP_3$ blocked by suitable protecting groups, thus eliminating the possibility of phosphate randomization during the delivery process. This improves the efficiency and isomeric specificity of $IP_3$ delivery. The hydrolysis product of IP3-CPM, i.e. caged $IP_3$ (V-16), was fairly resistant to phosphatase degradation. UV exposure of the HEK cells loaded with $IP_3$-CPM 6 hours previously still gave full-scale $[Ca^{2+}]_i$ increases. These properties are useful for various biological applications. In addition, $IP_3$-CPM was found to be chemically more stable than commercially available caged $IP_3$ where one of the vicinal 4- or 5-phosphates is randomly masked by one NPE group.

Permeant inositol polyphosphate derivatives as described above are useful to investigate longer-term effects on cells not mediated through cytosolic $[Ca^{2+}]_i$. For example, possible effects on protein synthesis, phosphorylation, proliferation (49), or gene expression are relatively difficult to study on microinjected, patch-clamped, or permeabilized cells.

Inositol polyphosphates are among the most ubiquitous and important intracellular second messengers. They are essential for hormone secretion and action, smooth muscle contraction, immune activation, fertilization, and neuronal function. As previously mentioned, the best known inositol polyphosphate is myo-inositol-1,4,5-triphosphate ($IP_3$), which acts by releasing $Ca^{2+}$ from intracellular stores. $IP_3$ undergoes further metabolism to a series of inositol polyphosphates of largely unknown biochemical function. A major problem in investigating the biological functions of inositol polyphosphates is their membrane impermeability. All existing techniques for delivering exogenous inositol polyphosphates into cells require puncture of their plasma membranes by techniques that jeopardize the cells' viability and are often applicable only to single cells. The inositol polyphosphate derivatives in accordance with the present invention provide a solution of this problem because they are membrane-permeant and they regenerate into biologically active inositol polyphosphates once inside the cell.

The acyloxyalkyl esters of phosphate-containing second messengers in accordance with the present invention may be used in any situation where it is desirable to introduce the second messenger into a cell without puncturing the cell membrane or otherwise adversely affecting the cell. The present invention is useful as a replacement for the existing methods which rely on microinjection, patch-clamp and electroporation techniques to introduce phosphate-containing second messengers into cells.

The acyloxyalkyl esters are introduced into the selected cells by simply exposing the cells to the esters-in cell growth media or other suitable solution. The amount of ester which is introduced into the cell can be controlled by reducing or increasing the concentration of ester present in the cell growth media. The amount of ester which permeates into the cell may also be controlled by limiting the amount of time that the cells are left exposed to the ester.

When using caged compounds, the additional step of exposing the cells to UV radiation is required. UV light at wavelengths around 360 nm is preferred. However, other wavelengths within the UV spectrum may be used provided that the selected wavelength is sufficient to uncage the protected compounds. The particular wavelength and degree of exposure required to uncage the protected compounds can be established for each case using well known procedures for exposing cells to UV radiation.

Having thus described exemplary embodiments of the present invention, it will be understood by those skilled in the art that the within disclosures are exemplary only and that the invention is only limited by the following claims.

BIBLIOGRAPHY

1. Hardie, D. G.(1991) *Biochemical Messengers: Hormones, Neurotransmitters and Growth Factors*, Champman & Hall, London.
2. Robinson, G. A., Butcher, R. W., and Sutherland, E. W. (1971) *Cyclic AMP*, Academic Press, New York.
3. Corbin, J. D., Johnson, R. A., eds (1988) *Methods in Enzymology: Initiation and Termination of Cyclic Nucleotide Action*, Academic Press, Inc., San Diego.
4. Goy, M. F.(1991) *Trends Neurosci.* 14, 293–299.
5. Berridge, M. J. and Irvine, R. F. (1989) *Nature* 341, 197–205.
6. Meyer, R. B., Jr. (1980) in *Burger's Medicinal Chemistry* (Wolff, M. E., ed.) pp. 1201–1224, Wiley, New York.
7. Polokoff, M. A., Bencen, G. H., Vacca, J. P., deSolms, S. J., Young, S. D., and Huff, J. R. (1988) *J. Biol. Chem.* 263, 11922–11927.
8. Henion, W. F., Sutherland, E. W., and Posternak, T. (1967) *Biochim. Biophys. Acta* 148, 106–113.
9. Roche, E. B., ed. (1987) *Bioreversible Carriers in Drug Design Pergamon* Press, New York.
10. Falbriard, J.-G., Posternak, T., and Sutherland, E. W. (1967) *Biochim. Biophys. Acta* 148, 99–105.
11. Jansen, A. B. A. and Russell, T. J. (1965) *J. Chem. Soc.* 2127–2132.
12. Tsien, R. Y.(1981) *Nature* 290, 527–528.
13. Grynkiewicz, G., Poenie, M., and Tsien, R. Y. (1985) *J. Biol. Chem.* 260, 3440–3450.
14. Tsien, R. Y.(1989) *Methods Cell Biol.* 30, 127–156.
15. Srivastva, D. N. and Farquhar, D. (1984) *Bioorg. Chem.* 12, 118–129.
16. Iyer, R. P., Phillips, L. R., Biddle, J. A., Thakker, D. R., Egan, W., Aoki, S., and Mitsuga, H. (1989) *Tetrahedron Lett.* 30, 7141–7144.
17. Sastry, J. K., Nehete, P. N., Khan, S., Nowak, B. J., Plunkett, W., Arlinghaus, R. B., and Farquhar, D. (1992) *Mol. Pharmacol.* 41, 441–445.

18. Freed, J. J., Farquhar, D., and Hompton, A. (1989) *Biochem. Pharmacol.* 38, 3193–3198.
19. Saperstein, R., Vicario, P. P., Strout, H. V., Brady, E., Slater, E. E., Greenlee, W. J., Ondeyka, D. L., Patchett, A. A., and Hangauer, D. G. (1989) *Biochemistry* 28, 5694–5701.
20. Walker, J. W., Reid, G. P., McCray, J. A., and Trentham, D. R. (1988) *J. Am. Chem. Soc.* 110, 7170–7177.
21. Nerbonne, J. M., Richard, S., Nargeot, J., and Lester, H. A. (1984) *Nature* 310, 74–76.
22. Engels, J. and Schlaeger, E. -J. (1977) *J. Med. Chem.* 20, 907–911.
23. Walker, J. W., Feeney, J., and Trentham, D. R. (1989) *Biochemistry* 28, 3272–3280.
24. Gurney, A. M. and Lester, H. A. (1987) *Physiol. Rev.* 67, 583–617.
25. McCray, J. A. and Trentham, D. R. (1989) *Annu. Rev. Biophys. Biophys. Chem.* 18, 239–270.
26. Berridge, M. J. and Irvine, R. F. (1989) *Nature* 341, 197–205.
27. Irvine, R. F. and Moor, R. M. (1986) *Biochem. J.* 240, 917–920.
28. Irvine, R. F. (1990) *FEBS Letters* 263, 5–9.
29. Morris, A. P., Gallacher, D. V., Irvine, R. F., and Petersen, O. H. (1987) *Nature* 330, 653–655.
30. Changya, L., Gallacher, D. V., Irvine, R. F., Potter, B. V. L., and Petersen, O. H. (1989) *J. Membrane Biol.* 109, 85–93.
31. Boynton, A. L., Dean, N. M., and Hill, T. D. (1990) *Biochem. Pharmacol.* 40, 1933–1939.
32. Hill, T. D., Dean, N. M., and Boynton, A. L. (1988) *Science* 242, 1176–1178.
33. Crossley, I., Swann, K., Chambers, E., and Whitaker, M. (1988) *Biochem. J.* 252, 257–262.
34. Snyder, P. M., Krause, K.-H., and Welsh, M. J. (1988) *J. Biol. Chem.* 263, 11048–11051.
35. Tsien, R. W. and Tsien, R. Y. (1990) *Annu. Rev. Cell Biol.* 6, 715–760.
36. Bird, G. St J., Rossier, M. F., Hughes, A. R., Shears, S. B., Armstrong, D. L., and Putney, Jr., J. W. (1991) *Nature* 352, 162–165.
37. Balla, T., Sim, S. S., Iida, T., Choi, K. Y., Catt, K. J., and Rhee, S. G. (1991) *J. Biol. Chem.* 266, 24719–24726.
38. Grynkiewicz, G. and Tsien, R. Y. (1987) *Pol. J. Chem.* 61, 443–447.
39. Adams, S. R., Harootunian, A. T., Buechler, Y. J., Taylor, S. S., and Tsien, R. Y. (1991) *Nature* 349, 694–697.
40. Dharmsathaporn, K., Mandel, K. G., Masui, H., and McRoberts, J. A. (1985) *J. Clin. Invest.* 75, 462–470.
41. Madara, J. and Dharmsathaporn, K. (1985) *J. Cell Biol.* 101, 2124–2133.
42. Dharmsathaporn, K., Mandel, K. G., McRoberts, J. A., Tisdale, L. D., and Masui, H. (1984) *Am. J. Physiol.* 264, G204–G208.
43. McRoberts, J. A. and Barrett, K. E. (1989) *Modern Cell Biology* (Mathi, K. S. and Valeulich, J. D., eds) pp. 235–265, Alan R. Liss, Inc., New York.
44. Sammak, P. J., Adams, S. R., Harootunian, A. T., Schliwa, M., and Tsien, R. Y. (1992) *J. Cell Biol.* 117, 57–72.
45. Taylor, S. S., Buechler, J. A., and Yonemoto, W. (1990) *Annu. Rev. Biochem.* 59, 971–1005.
46. Barrett, K. E. and Dharmsathaporn, K. (1991) *Textbook of Gastroenterology* (Yamada, T., ed) pp. 265–294, J. B. Lippincott Co., Philadelphia.
47. Schliwa, M. (1975) *Microtubules and Microtubule Inhibitors* (Borgers, M. and de Brabender, M., eds) pp. 215–228, Elsevier Science, Amsterdam.
48. Beebe, S. J., Blackmore, P. F., Chrisman, T. D., and Corbin, J. D. (1988) *Methods Enzymol.* 159, 118–139.
49. Smirnova, L. I., Malenkovskaya, N. A, Preddoditelev, D. A., and Nifant'ev, E. E. (1980) *Zh. Org. Khim.* 16, 1011–1019.
50. Angyal, S. J. and Tate, M. E. (1965) *J. Chem. Soc.* 6949–6955.
51. Tegge, W. (1986) *Ph. D. Thesis University* of Bremen-FRG.
52. Lee, H. W. and Kishi, Y. (1985) *J. Org. Chem.* 50, 4402–4404.
53. Billington, D. C., Baker, R., Kulagowski, J. J., Mawer, I. M., Vacca, J. P., deSolms, S. J., and Hugg, J. R. (1989) *J. Chem. Soc. Perkin Trans.* 1 1423–1429.
54. Baudin, G., Glanzer, B. I., Swaminathan, K. S., and Vasella, A. (1988) *Helv. Chim. Acta* 71; 1367–1378.
55. Tegge, W. and Ballou, C. E. (1989) *Proc. Natl. Acad. Sci. USA* 86, 94–98.
56. Perich, J. W. and Johns, R. B. (1987) *Tetrahedron Lett.* 28, 101–102.
57. Thastrup, O., Cullen, P. J., Drobak, B. K., Hanley, M. R., and Dawson, A. P. (1990) *Proc. Natl. Acad. Sci. USA* 87, No. 7, 2466–2470.
58. Tsien, R. Y. and Harootunian, A. T. (1990) *Cell Calcium* 11, 93–109.
59. Harootunian, A. T., Kao, J. P. Y., Paranjape, S., Adams, S. R., Potter, B. V. L., and Tsien, R. Y. (1991) *Cell Calcium* 12, 153–164.
60. Harootunian, A. T., Kao, J. P. Y., Paranjape, S., and Tsien, R. Y. (1991) *Science* 251, 75–78.
61. Finch, E. A., Turner, T. J., and Goldin, S. M. (1991) *Scient* 252, 443–446.
62. Kuno, M. and Gardner, P. (1987) *Nature* 236, 301–304.
63. Penner, R., Matthews, G., and Neher, E. (1988) *Nature* 334, 499–504.
64. Schultz, C. et al. (1993) *Journal of Biological Chemistry* Vol. 268, No. 9, 6316–6322.
65. Oozaki, S. et al., *Tetrahedron Lett.* 27 (1986), 3157; Dreef, C. E. et al., *Rec. Trav. Chim. Pays-Bas.* 107 (1988), 395.
66. Billington, D. C. et al., *J. Chem. Soc. Chem. Communications* (1987), 101 1; Baudin, G. et al., *Helv. Chim. Acta* 71 (1988) 1367.
67. Kozikowski, A. P. et al., *J. Am. Chem. Soc.* 115 (1993), 4429.
68. Kozikowski, A. P. et al., *J. Am. Chem. Soc.* 112 (1990), 7403.
69. Bannwarth, W. et al., *Helv. Chim. Acta.* 70 (1987), 175.
70. Euranto, E. K. et al., *Acta. Chem. Scand.* 20 (1966), 1273.
71. Randriamampita, C and Tsien, R. Y. (1993) *Nature* 364:809–814.
72. McCray, J. A. & Trentham, D. R. (1989) *Annu. Rev. Biophys. Biophys. Chem.* 18, 239–270.
73. Adams, S. R. & Tsien, R. Y. (1993) *Annu. Rev. Physiol.* 55, 755–784.
74. Walker, J. W., Reid, G. P. & Trentham, D. R. (1989) *Methods Enzymol.* 172, 288–301.
75. Wootton, J. F. &Trentham, D. R. (1989) *NATO ASI Ser.* C 272
76. Lev-Ram, V., Makings, L. R., Keitz, P. F., Kao, J. P. & Tsien, R. Y. (1995) *Neuron* 15, 407–415.
77. Makings, L. R. & Tsien, R. Y. (1994) *J. Biol. Chem.* 269, 6282–6285.
78. Krafft, G. A., Sutton, W. R. & Cummings, R. T. (1988) *J. Am. Chem. Soc.* 110, 301.
79. Adams, S. R., Kao, J. P. Y. & Tsien, R. Y. (1988) *J. Am. Chem. Soc.* 110, 3212.

80. Tsien, R. Y. & Zucker, R. S. (1986) *Biophys. J.* 50, 843–853.
81. Callaway, E. M. & Katz, L. C. (1993) *Proc. Natl. Acad. Sci U.S.A.* 90, 7661–7665.
82. Wilcox, M., Viola, R. W., Johnson, K. W., Billington, A. P., Carpenter, B. K., McCray, J. A., Guzikowski, A. P. & Hess, G. P. (1990) *J. Org. Chem.* 55, 1585.
83. Corrie, J. E., DeSantis, A., Katayama, Y., Khodakhah, K., Messenger, J. B., Ogden, D. C. & Trentham, D. R. (1993) *J. Physiol. (Lond)* 465, 1–8.
84. Walker, J. W., Somlyo, A. V., Goldman, Y. E., Somlyo, A. P. & Trentham, D. R. (1987) *Nature* 327, 249–252.
85. Walker, J. W., Feeney, J. & Trentham, D. R. (1989) *Biochemistry* 28,3272–3280.
86. Greene, T. W. & Wuts, P. G. M. (1991) *Protective Groups in Organic Synthesis*, John 219 Wiley & Sons: New York
87. Hanessian, S. & Roy, R. (1985) *Can. J. Chem.* 63, 163.
88. Yu, K. & Fraser-Reid, B. (1988) *Tetrahedron Lett.* 26, 979.
89. Yu, K., Ko, K. & Fraser-Reid, B. (1988) *Synthetic Comm.* 18, 465.
90. Buncel, E. (1984) *Electron Deficient Aromatic- and Heteroaromatic-Base Interactions*, Elsevier: New York
91. Vacca, J. P., Jane deSolms, S., Huff, J. R., Billington, D. C., Baker, R., Kulagowski, J. J. & Mawer, I. M. (1989) *Tetrahedron* 45, 5679
92. Asmis, R., Randriamampita, C., Tsien, R. Y. & Dennis, E. A. (1994) *Biochem. J.* 298, 543.
93. Garegg, P., Iverson, T., Johansson, R. & Lindberg, B. (1984) *Carbohydr. Res.* 130, 322.

What is claimed is:
1. A compound having the formula

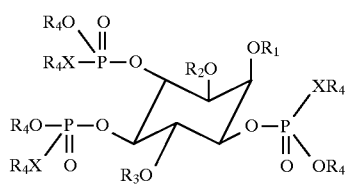

wherein $R_1$ is H, —CHO, COOCH$_3$ or —COCH$_3$; $R_2$ is H or —P(O)(OR$_4$)(XR$_4$); or $R_1$ and $R_2$ together are —CH$_2$—, —CHMe—, —CMe$_2$—, —CH(OMe)—, —CMe(OMe)— or —C(OMe)$_2$—; $R_3$ is a photolabile protecting group selected from the group consisting of

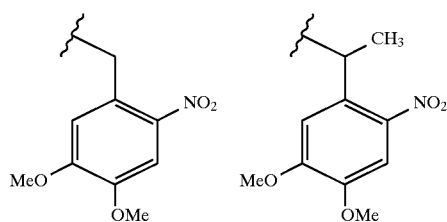

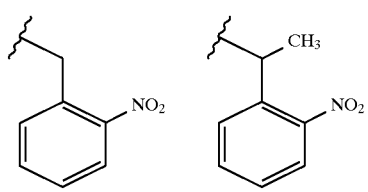

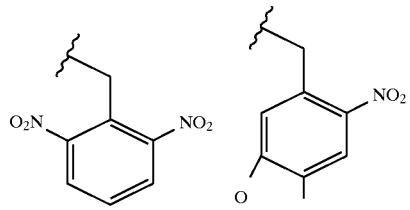

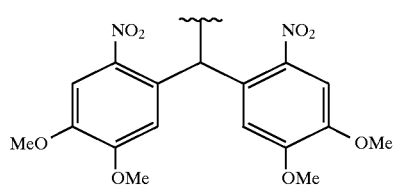

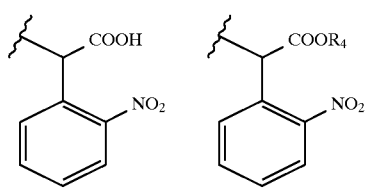

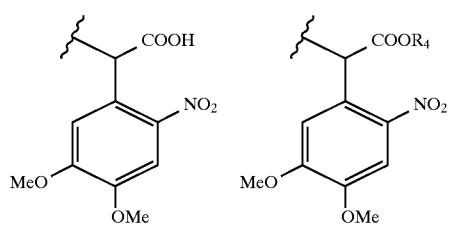

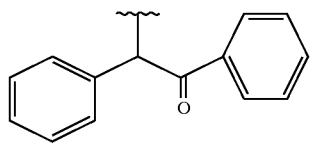

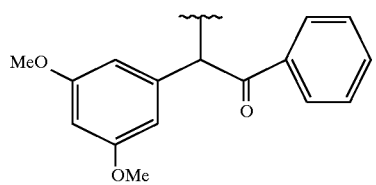

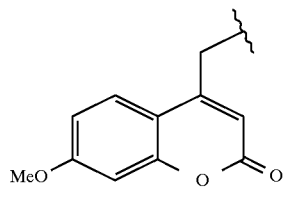

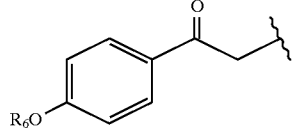

wherein $R_6$=H, Me, CH$_3$CO;

$R_4$ is

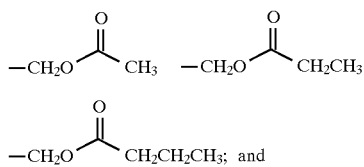

X is O or S.

2. A compound according to claim 1 wherein X is O.

3. A compound according to claim 2 wherein $R_1$ and $R_2$ together are —CH(OMe).

4. A compound according to claim 2 wherein $R_3$ is

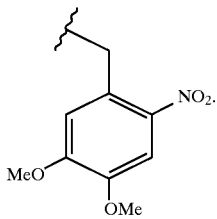

5. A compound according to claim 2 wherein $R_4$ is

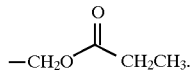

6. A compound according to claim 4 wherein $R_4$ is

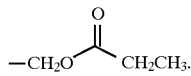

7. A compound according to claim 3 wherein R4 is

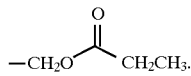

8. A compound according to claim 3 wherein $R_3$ is

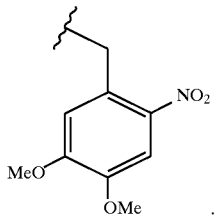

9. A compound according to claim 8 wherein $R_4$ is

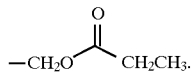

10. A method for introducing phosphate-containing second messengers into a cell without disrupting the cell membrane, said method comprising the steps of:

contacting said cell with a compound having the formula

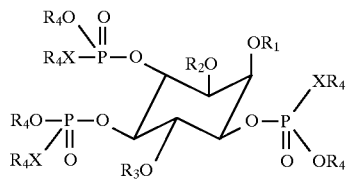

wherein $R_1$ is H, —CHO, COOCH$_3$ or —COCH$_3$; $R_2$ is H or —P(O)(OR$_4$)(XR$_4$); or $R_1$ and $R_2$ together are —CH$_2$—, —CHMe—, —CMe$_2$—, —CH(OMe)—, —CMe(OMe)— or —C(OMe)$_2$—; $R_3$ is a photolabile protecting group selected from the group consisting of

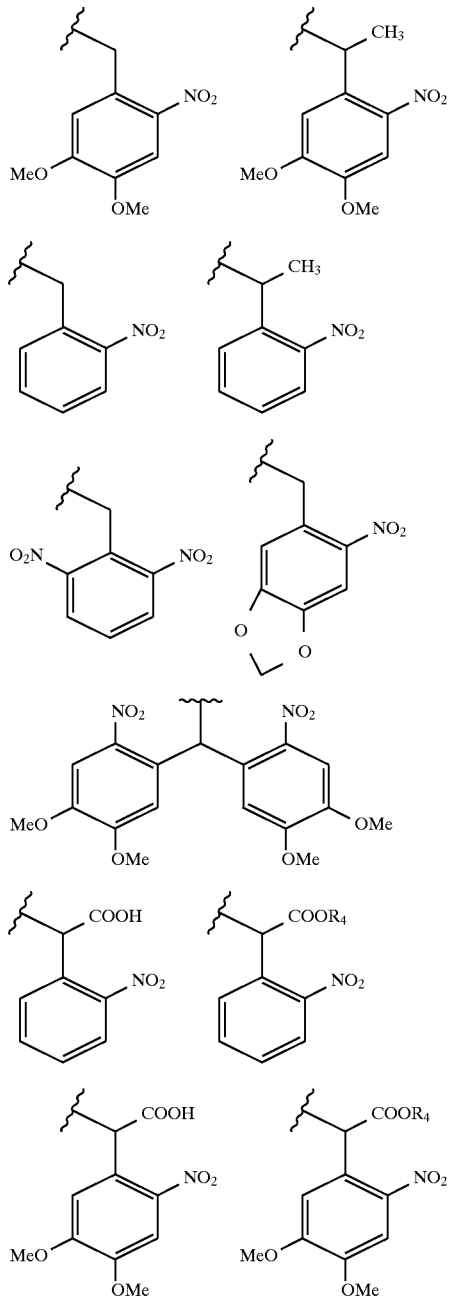

-continued

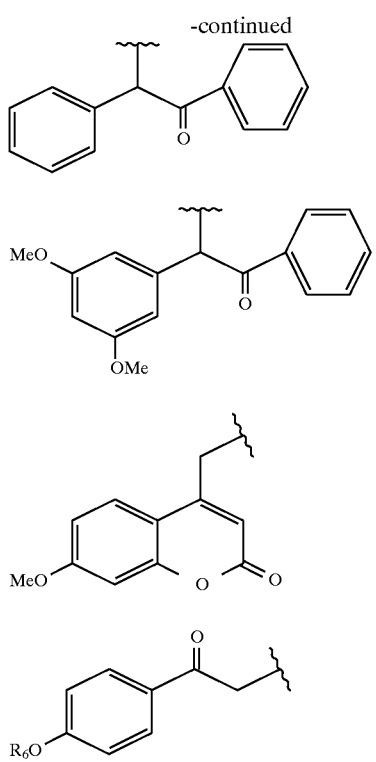

wherein $R_6$=H, Me, $CH_3CO$;

$R_4$ is

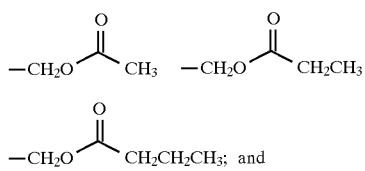

X is O or S;

said contact being for a sufficient time to provide permeation of said caged compound into said cell; and exposing said cell to a sufficient amount of ultraviolet radiation for a sufficient time to uncage said caged compound.

11. A method according to claim 10 wherein X is O.

12. A method according to claim 11 wherein $R_4$ is

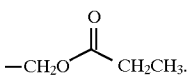

13. A method according to claim 11 wherein $R_1$ and $R_2$ together are —CH(OMe).

14. A method according to claim 11 wherein $R_3$ is

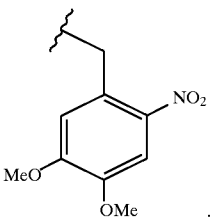

15. A method according to claim 14 wherein $R_4$ is

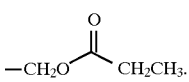

16. A compound according to claim 13 wherein R4 is

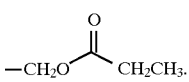

17. A method according to claim 13 wherein $R_3$ is

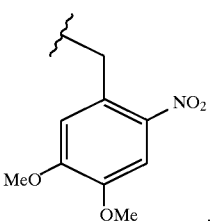

18. A compound according to claim 17 wherein $R_4$ is

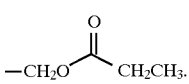

* * * * *